United States Patent
Dobak

(10) Patent No.: US 9,687,455 B2
(45) Date of Patent: Jun. 27, 2017

(54) SODIUM TETRADECYL SULFATE FORMULATIONS FOR TREATMENT OF ADIPOSE TISSUE

(71) Applicant: John Daniel Dobak, La Jolla, CA (US)

(72) Inventor: John Daniel Dobak, La Jolla, CA (US)

(*) Notice: Subject to any disclaimer, the term of this patent is extended or adjusted under 35 U.S.C. 154(b) by 0 days.

(21) Appl. No.: 14/827,083

(22) Filed: Aug. 14, 2015

(65) Prior Publication Data

US 2016/0045452 A1  Feb. 18, 2016

Related U.S. Application Data

(60) Provisional application No. 62/037,272, filed on Aug. 14, 2014.

(51) Int. Cl.
| | | |
|---|---|---|
| A61K 31/095 | (2006.01) |
| A61K 31/00 | (2006.01) |
| A61K 9/00 | (2006.01) |
| A61K 8/46 | (2006.01) |
| A61Q 19/06 | (2006.01) |

(52) U.S. Cl.
CPC ............ *A61K 31/095* (2013.01); *A61K 8/463* (2013.01); *A61K 9/0019* (2013.01); *A61K 31/00* (2013.01); *A61Q 19/06* (2013.01); *A61K 2800/91* (2013.01)

(58) Field of Classification Search
CPC .... A61K 31/095; A61K 8/463; A61K 9/0019; A61K 31/00
USPC ........................................................ 514/711
See application file for complete search history.

(56) References Cited

U.S. PATENT DOCUMENTS

| | | | |
|---|---|---|---|
| 5,614,178 A | 3/1997 | Bloom et al. |
| 5,676,962 A | 10/1997 | Cabrera et al. |
| 5,681,552 A | 10/1997 | Shevade et al. |
| 5,756,119 A | 5/1998 | Deckner et al. |
| 5,874,095 A | 2/1999 | Deckner et al. |
| 6,572,873 B1 | 6/2003 | Osman et al. |
| 6,846,412 B2 | 1/2005 | Hogan et al. |
| 6,942,165 B1 | 9/2005 | Osman et al. |
| RE38,919 E | 12/2005 | Garrido et al. |
| 7,025,290 B2 | 4/2006 | Osman et al. |
| 7,026,360 B1 | 4/2006 | Festo |
| 7,166,570 B2 | 1/2007 | Hunter et al. |
| 7,357,336 B2 | 4/2008 | Osman et al. |
| RE40,640 E | 2/2009 | Garrido et al. |
| 7,494,488 B2 | 2/2009 | Weber |
| 7,604,185 B2 | 10/2009 | Osman et al. |
| 7,622,130 B2 | 11/2009 | Kolodney et al. |
| 7,727,537 B2 | 6/2010 | Modi |
| 7,731,986 B2 | 6/2010 | Wright et al. |
| 7,754,230 B2 | 7/2010 | Kolodney et al. |
| 7,814,943 B2 | 10/2010 | Harman et al. |
| 7,842,282 B2 | 11/2010 | Harman et al. |
| 7,842,283 B2 | 11/2010 | Harman et al. |
| 7,902,387 B2 | 3/2011 | Prasad et al. |
| 7,994,351 B2 | 8/2011 | Prasad et al. |
| 8,101,593 B2 | 1/2012 | Hodge et al. |
| 8,122,917 B2 | 2/2012 | Harman et al. |
| 8,242,294 B2 | 8/2012 | Moriarty et al. |
| 8,298,556 B2 | 10/2012 | Kolodney et al. |
| 8,323,677 B2 | 12/2012 | Wright et al. |
| 8,362,285 B2 | 1/2013 | Prasad et al. |
| 8,367,649 B2 | 2/2013 | Hodge et al. |
| 8,367,852 B2 | 2/2013 | Prasad et al. |
| 8,734,833 B2 | 5/2014 | Wright et al. |
| 8,808,716 B2 | 8/2014 | Loupenok |
| 8,846,066 B2 | 9/2014 | Kolodney et al. |
| 2003/0147928 A1 | 8/2003 | Zelle et al. |
| 2003/0216364 A1 | 11/2003 | Johnson |
| 2005/0089555 A1 | 4/2005 | Boderke et al. |
| 2005/0106544 A1 | 5/2005 | Joshi et al. |
| 2005/0143347 A1 | 6/2005 | Boderke et al. |
| 2005/0238705 A1 | 10/2005 | Hu et al. |
| 2005/0255149 A1 | 11/2005 | Narui et al. |
| 2006/0110448 A1 | 5/2006 | Grassberger et al. |
| 2006/0127468 A1 | 6/2006 | Kolodney et al. |
| 2006/0154906 A1 | 7/2006 | Kolodney et al. |
| 2006/0190299 A1 | 8/2006 | Joshi et al. |
| 2008/0069779 A1 | 3/2008 | Tamarkin et al. |
| 2008/0187595 A1 | 8/2008 | Jordan et al. |
| 2008/0193541 A1 | 8/2008 | Mentrup et al. |
| 2008/0206155 A1 | 8/2008 | Tamarkin et al. |
| 2008/0268055 A1 | 10/2008 | Mentrup et al. |
| 2008/0286349 A1 | 11/2008 | Nomoto et al. |

(Continued)

FOREIGN PATENT DOCUMENTS

| | | |
|---|---|---|
| CA | 2543187 A1 | 5/2005 |
| CA | 2741334 A1 | 4/2010 |

(Continued)

OTHER PUBLICATIONS

Berge et al. Pharmaceutical Salts, Journal of Pharmaceutical Sciences 66(1):1-19 (Jan. 1977).
Co-pending U.S. Appl. No. 14/827,071, filed Aug. 4, 2015.
Ethamolin® Product Label. QOL Medical, LLC. (2012).
Human Prescription Drug Label for ASCLERA—polidocanol injection, solution; Updated C; Accessed from: http://dailymed.nlm.nih.gov/dailymed/drugInfo.cfm?setid=90550274-6605-44de-8c25-c5591080270f on Sep. 30, 2014.
INEOS Oxide (lauryl Alcohol Ethoxylates, http://www.ineos.com/Show-Document/?Grade=Alkyr/020Ether)/020AE7&BU=INEOS°/0200xide&DocumentType=Technicar/020Date/020Sheet, obtained from internet Mar. 19, 2015).
Scientific Committee on Consumer Products (Opinion on polidocanol, SCCP 13th plenary meeting, published Oct. 2, 2007).
Sotradecol® Product Label. Bioniche Pharma Group Limited (2004).

(Continued)

*Primary Examiner* — Yevegeny Valenrod
(74) *Attorney, Agent, or Firm* — Wilson Sonsini Goodrich & Rosati

(57) ABSTRACT

Contained herein are compositions, formulations, methods, and kits for treating regional fat deposits and fat-related conditions. Certain methods comprise administering tetradecyl sulfate, tetradecyl sulfate-like compounds, and pharmaceutically or cosmetically acceptable salts, solvates, prodrugs, or esters thereof and a liquid carrier.

23 Claims, No Drawings

(56) References Cited

U.S. PATENT DOCUMENTS

| | | |
|---|---|---|
| 2008/0294072 A1 | 11/2008 | Crutchfield, III |
| 2009/0202467 A1 | 8/2009 | Bock |
| 2009/0214657 A1 | 8/2009 | Qazi et al. |
| 2010/0011890 A1 | 1/2010 | Tseng |
| 2010/0062067 A1 | 3/2010 | Tonge et al. |
| 2010/0098766 A1 | 4/2010 | Mentrup et al. |
| 2010/0137747 A1 | 6/2010 | Thomas et al. |
| 2010/0144890 A1 | 6/2010 | Boderke et al. |
| 2010/0166681 A1 | 7/2010 | Franke |
| 2010/0292650 A1 | 11/2010 | Kolodney et al. |
| 2011/0002896 A1 | 1/2011 | Kolodney et al. |
| 2011/0082124 A1* | 4/2011 | Burkhart ............... A61K 31/13 514/171 |
| 2012/0009285 A1 | 1/2012 | Wei et al. |
| 2012/0016347 A1 | 1/2012 | Shipp et al. |
| 2012/0141531 A1 | 6/2012 | Coulter et al. |
| 2012/0283328 A1 | 11/2012 | Modi |
| 2012/0329765 A1 | 12/2012 | Boderke et al. |
| 2013/0143869 A1 | 6/2013 | Kiehm et al. |
| 2013/0190282 A1 | 7/2013 | Hodge et al. |
| 2013/0190517 A1 | 7/2013 | Prasad et al. |
| 2013/0267721 A1 | 10/2013 | Prasad et al. |
| 2013/0331332 A1 | 12/2013 | Barg et al. |
| 2014/0155364 A1 | 6/2014 | Hodge et al. |

FOREIGN PATENT DOCUMENTS

| | | |
|---|---|---|
| EP | 1748780 A1 | 2/2007 |
| EP | 1758590 A1 | 3/2007 |
| EP | 1845938 A1 | 10/2007 |
| EP | 1946746 A1 | 7/2008 |
| EP | 1970051 A1 | 9/2008 |
| EP | 2369956 A1 | 10/2011 |
| EP | 2380576 A2 | 10/2011 |
| EP | 2422789 A1 | 2/2012 |
| EP | 2550968 A1 | 1/2013 |
| EP | 2572718 A1 | 3/2013 |
| WO | WO-9812228 A1 | 3/1998 |
| WO | WO-2005041919 A2 | 5/2005 |
| WO | WO-2010048409 A1 | 4/2010 |
| WO | WO-2010106076 A1 | 9/2010 |
| WO | WO-2013079211 A1 | 6/2013 |

OTHER PUBLICATIONS

U.S. Appl. No. 14/506,540 Office Action dated Apr. 3, 2015.

Fu et al. Oleoylethanolamide, an endogenous PPAR-alpha agonist, lowers body weight and hyperlipidemia in obese rats. Neuropharmacology 48(8):1147-1153 (2005).

Lemaire. The flow of venous blood in the obese. Phlebologie 41(3):493-499 (1988) (Abstract).

Meyer. Monoethanolamine Oleate. A New Chemical for the Obliteration of Varicose Veins. American Journal of Surgery. 40(3):628-629 (1938).

U.S. Appl. No. 14/827,071 Office Action dated Mar. 9, 2017.

* cited by examiner

SODIUM TETRADECYL SULFATE FORMULATIONS FOR TREATMENT OF ADIPOSE TISSUE

CROSS-REFERENCE

This application claims the benefit of U.S. Provisional Application No. 62/037,272 filed Aug. 14, 2014, which is incorporated herein by reference.

BACKGROUND

Surgical and non-surgical procedures for improving appearance have increased in prevalence as populations age and gain weight. Liposuction is a popular cosmetic surgery procedure and involves the surgical removal of fat deposits using suction and optionally assisted by solutions to assist in fat removal. Liposuction is a surgical procedure that removes fat through an incision in the skin through which a cannula is inserted. The cannula is connected to a suction source and the unwanted fat is aspirated through the cannula and discarded. Liposuction is performed under general or local anesthesia, depending on the amount and location of the fat to be removed. However, liposuction and other surgical methods of fat removal are associated with significant adverse events including temporary bruising, swelling, numbness, soreness and burning sensation, risk of infection, pigmentation changes, the formation of fat clots or blood clots which can migrate to the lungs and cause death, excessive fluid loss, which can lead to shock or fluid accumulation that must be drained, friction burns or other damage to the skin or nerves or perforation injury to the vital organs. Additionally, liposuction requires a recovery time of one to two weeks wherein the patient cannot work or perform certain daily activities. Moreover, because surgical procedures such as liposuction require local and occasionally general anesthesia, significant anesthesia-related risks are associated with surgical fat removal (including, e.g., loose and flabby skin) Furthermore, in certain situations liposuction and other drastic weight loss methods can be life threatening to the patient.

Accumulation of fat stores can occur unevenly in the body. For example, some persons may accumulate fat predominantly in the abdominal cavity while others predominately in the subcutaneous tissue. Gender differences may also be apparent with women accumulating fat in the thighs and lateral buttocks and males in the waist. Women may accumulate fatty deposits of the thighs, which have a rumpled or "peau-de-orange" appearance, resulting in a condition referred to as cellulite. Cellulite may be related to skin architecture which allows subdermal fat herniation, sometimes referred to as adipose papillae. Other factors that may be related to cellulite include altered and/or reduced connective tissue septae, vascular and lymph changes that lead to fluid accumulation, and inflammation. Fat tissue may also accumulate in the form of a fibrous fatty deposit known as a lipoma. Lipomas are tumors of fatty tissues, generally benign. If malignant, they are known as liposarcomas. Benign lipomas contain normal fat that is encapsulated within a fibrous sphere, thus often compressing the fat and causing it to feel more firm than surrounding fat. Many lipomas are asymptomatic and are removed for non-medical reasons. However, a significant number of them cause the patient pain or discomfort and they interfere with normal activity.

SUMMARY

Described herein are compositions, methods, and kits for reducing and/or eliminating subcutaneous fat deposits. Provided herein, in certain embodiments, are injectable formulations for treating regional adipose tissue, regional adiposity, or regional fat accumulation. In certain embodiments, the formulations comprise an effective amount of tetradecyl sulfate, tetradecyl sulfate-like compound, or a pharmaceutically or cosmetically acceptable salt, solvate, prodrug, or ester thereof and a liquid carrier; wherein the tetradecyl sulfate, tetradecyl sulfate-like compound, or a pharmaceutically or cosmetically acceptable salt, solvate, prodrug, or ester thereof and a liquid carrier are formulated for injection into a layer of subcutaneous fat for a human in need thereof. In some embodiments, the tetradecyl sulfate, tetradecyl sulfate-like compound, or a pharmaceutically or cosmetically acceptable salt, solvate, prodrug, or ester thereof is sodium tetradecyl sulfate. In some embodiments, the tetradecyl sulfate, tetradecyl sulfate-like compound, or a pharmaceutically or cosmetically acceptable salt, solvate, prodrug, or ester thereof is potassium tetradecyl sulfate. In some embodiments of these formulations, provided herein is a glucocorticosteroid or a pharmaceutically or cosmetically acceptable salt, solvate, prodrug, or ester thereof. Some embodiments also comprise a bile acid such as deoxycholic acid or a pharmaceutically or cosmetically acceptable salt, solvate, prodrug, or ester thereof. In certain embodiments, the formulation is an extended release formulation. In further embodiments, the formulation is a rapid-release formulation. In some embodiments, the therapeutically effective amount of tetradecyl sulfate (including for example sodium and potassium salt forms) or tetradecyl sulfate-like compound is released for about 12 hours to about 45 days (e.g., about 3 days to about 10 days).

In certain embodiments, provided herein is an injectable formulation for treating regional adipose tissue, regional adiposity, or regional fat accumulation comprising: an effective amount of the compound of Formula I

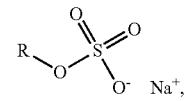

or a pharmaceutically or cosmetically acceptable salt, solvate, prodrug, or ester thereof, R is a saturated, linear $C_7$-$C_{24}$ hydrocarbon, or an unsaturated, linear $C_7$-$C_{24}$ hydrocarbon; and a liquid carrier; the compound of Formula I, or a pharmaceutically or cosmetically acceptable salt, solvate, prodrug, or ester thereof, and a liquid carrier formulated for injection into a layer of subcutaneous fat for a human in need. In certain embodiments, R is a saturated, linear $C_7$-$C_{24}$ hydrocarbon. In an embodiment, R is an unsaturated, linear $C_7$-$C_{24}$ hydrocarbon. In some embodiments, R is a saturated, linear $C_7$-$C_{12}$ hydrocarbon. In some embodiments, R is a saturated, linear $C_{12}$-$C_{18}$ hydrocarbon. In an embodiment, R is a saturated, linear $C_{18}$-$C_{24}$ hydrocarbon. In some embodiments, R is an unsaturated, linear $C_7$-$C_{12}$ hydrocarbon. In an embodiment, R is an unsaturated, linear $C_{12}$-$C_{18}$ hydrocarbon. In some embodiments, R is an unsaturated, linear $C_{18}$-$C_{24}$ hydrocarbon. In certain embodiments, the unsaturated, linear hydrocarbon comprises at least one alkene moiety. In some embodiments, the unsaturated, linear hydrocarbon comprises at least one alkene moiety of cis configuration. In certain embodiments, the unsaturated, linear hydrocarbon comprises at least one alkene moiety of trans configuration. In some embodiments, the unsaturated, linear hydrocarbon comprises at least one alkyne moiety.

In certain embodiments, the injectable formulation provided herein for treating regional adipose tissue, regional adiposity, or regional fat accumulation comprise an effective amount of the compound of Formula I

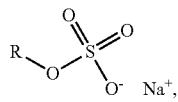

wherein R is a saturated or unsaturated, linear $C_{14}$ hydrocarbon. In certain embodiments, the unsaturated, linear hydrocarbon comprises at least one alkene moiety. In some embodiments, the unsaturated, linear hydrocarbon comprises at least one alkene moiety of cis configuration. In some embodiments, the unsaturated, linear hydrocarbon comprises at least one alkene moiety of trans configuration. In certain embodiments, the unsaturated, linear hydrocarbon comprises at least one alkyne moiety.

In some embodiments are methods and formulations that facilitate dispersal of tetradecyl sulfate, tetradecyl sulfate-like compounds, and salts, solvates, prodrugs, or esters thereof into a layer of subcutaneous fat at a regional fat site selected from one or more of the following: a submental region, an abdominal region, a waist, a hip, a lateral buttock, a thigh, a periorbital region, an intraorbital region, and intramuscular region. In certain embodiments is a formulation for the treatment of at least one of: abdominal adiposity, regional adiposity, or exophthalmos caused by thyroid eye disease. In certain embodiments are formulations that affect a shape, contour, or appearance of the human body.

In some embodiments, are injectable formulations for treating regional adipose tissue, regional adiposity, or regional fat accumulation, comprising an effective amount of Formula II, or a pharmaceutically or cosmetically acceptable salt, solvate, prodrug, or ester thereof, and a liquid carrier; wherein, the compound or a pharmaceutically or cosmetically acceptable salt, solvate, prodrug, or ester thereof and a liquid carrier is formulated for injection into a layer of subcutaneous fat for a human in need.

Formula II

In certain embodiments, a formulation described herein comprises a compound of Formula II. In certain embodiments, a formulation described herein comprises a compound of Formula II, or a pharmaceutically or cosmetically acceptable salt, solvate, prodrug, or ester thereof. In certain embodiments, a formulation described herein comprises tetradecyl sulfate, a tetradecyl sulfate-like compound, or a pharmaceutically or cosmetically acceptable salt, solvate, prodrug, or ester thereof. In some embodiments, a formulation described herein comprises sodium tetradecyl sulfate. In some embodiments, a formulation described herein comprises potassium tetradecyl sulfate. In certain embodiments, a formulation described herein is stable for a period of at least 6 months at a temperature of about 0° C. to about 50° C. In some embodiments, the formulation described herein also comprises a liquid carrier. In some embodiments, the liquid carrier is a lipophilic liquid carrier. In some embodiments, a formulation comprising a compound of Formula II described herein allows dispersal of the compound or salt, solvate, prodrug, or ester thereof into the layer of subcutaneous fat at a regional fat site selected from at least one of the following: a submental region, an abdominal region, a waist, a hip, a lateral buttock, a thigh, a periorbital region, an intraorbital region, and an intramuscular region.

In certain embodiments is a formulation wherein the compound of Formula I or Formula II, or a pharmaceutically or cosmetically acceptable salt, solvate, prodrug, or ester thereof is present in an amount that is equal to or less than about 10% weight/volume (W/V). In certain embodiments, the compound of Formula I or Formula II, or a pharmaceutically or cosmetically acceptable salt, solvate, prodrug, or ester thereof is present in an amount that is equal to or more than about 0.1% W/V to an amount that is equal to or less than about 10% W/V. In another embodiment, the compound or a pharmaceutically or cosmetically acceptable salt, solvate, prodrug, or ester thereof is present in an amount that is equal to or more than about 0.2% W/V to an amount that is equal to or less than about 8% W/V. Also provided are embodiments of the formulations described herein wherein the compound of Formula I or Formula II, or a pharmaceutically or cosmetically acceptable salt, solvate, prodrug, or ester thereof is present in an amount that is equal to or more than about 0.3% W/V to an amount that is equal to or less than about 6% W/V. In an embodiment, a compound or a pharmaceutically or cosmetically acceptable salt, solvate, prodrug, or ester thereof is present in an amount that is equal to or more than about 0.4% W/V to an amount that is equal to or less than about 4% W/V. In some embodiments, a compound of Formula I or Formula II, or a pharmaceutically or cosmetically acceptable salt, solvate, prodrug, or ester thereof is present in an amount that is equal to or more than about 0.5% W/V to an amount that is equal to or less than about 3% W/V. In a further embodiment of the formulations described herein, a compound of Formula I or Formula II, or a pharmaceutically or cosmetically acceptable salt, solvate, prodrug, or ester thereof is present in an amount that is greater than 3% W/V. In a further embodiment of the formulations described herein, a compound of Formula I or Formula II, or a pharmaceutically or cosmetically acceptable salt, solvate, prodrug, or ester thereof is present in an amount that is equal to about 3% W/V. In a further embodiment of the formulations described herein, a compound of Formula I or Formula II, or a pharmaceutically or cosmetically acceptable salt, solvate, prodrug, or ester thereof is present in an amount that is less than 3% W/V. In a further embodiment of the formulations described herein, a compound of Formula I or Formula II, or a pharmaceutically or cosmetically acceptable salt, solvate, prodrug, or ester thereof is present in an amount that is greater than 1% W/V. In a further embodiment of the formulations wherein a compound of Formula I or Formula II, or a pharmaceutically or cosmetically acceptable salt, solvate, prodrug, or ester thereof is present in an amount that is equal to about 1% W/V. In a further embodiment of the formulations described herein, a compound of Formula I or Formula II, or a pharmaceutically or cosmetically acceptable salt, solvate, prodrug, or ester thereof is present in an amount that is less than 1% W/V. In an embodiment, a compound of Formula I or Formula II, or a pharmaceutically or cosmetically acceptable salt, solvate prodrug, or ester thereof is present in an amount that is equal to about 0.5% W/V. In certain embodiments, the compound of Formula II is tetradecyl sulfate, a tetradecyl sulfate-like compound, or a pharmaceutically or cosmetically acceptable salt, solvate, prodrug, or ester thereof Yet another feature of the subject matter described herein is tetradecyl sulfate, a tetradecyl sulfate-like compound, or a pharmaceutically or cosmetically acceptable salt, solvate, prodrug, or ester thereof, in specific amounts for administration to patients. In an exemplary embodiment, a formulation comprises less than 20 mg of tetradecyl sulfate, a tetradecyl sulfate-like compound, or a pharmaceutically or cosmetically acceptable salt, solvate, prodrug, or ester thereof. In another exemplary embodiment, a formulation comprises 20 mg of tetradecyl sulfate, a tetradecyl sulfate-like compound, or a pharmaceutically or cosmetically acceptable salt, solvate, prodrug, or ester thereof. In another exemplary embodiment, a formulation comprises more than 20 mg of tetradecyl sulfate, a tetradecyl sulfate-like compound, or a pharmaceutically or cosmetically acceptable salt, solvate, prodrug, or ester thereof. In an exemplary embodiment, a formulation comprises less than 60 mg of tetradecyl sulfate, a tetradecyl sulfate-like compound, or a pharmaceutically or cosmetically acceptable salt, solvate, prodrug, or ester thereof. In another exemplary embodiment, a formulation comprises 60 mg of tetradecyl sulfate, a tetradecyl sulfate-like compound, or a pharmaceutically or cosmetically acceptable salt, solvate, prodrug, or ester thereof. In another exemplary embodiment, a formulation comprises more than 60 mg of tetradecyl sulfate, a tetradecyl sulfate-like compound, or a pharmaceutically or cosmetically acceptable salt, solvate, prodrug, or ester thereof. In some exemplary embodiments, a formulation comprises from about 0.1 mg to about 200 mg (e.g., about 0.5 mg, 1 mg, 1.5 mg, 2.0 mg, 2.5 mg, 3 mg, 3.5 mg, 4 mg, 4.5 mg, 5 mg, 5.5 mg, 6 mg, 6.5 mg, 7 mg, 8 mg, 9 mg, 10 mg, 15 mg, 20 mg, 25 mg, 50 mg, 75 mg, 80 mg, 85 mg, 90 mg, 95 mg, 100 mg, 105 mg, 110 mg, 115 mg, 120 mg, 125 mg, 150 mg, 175 mg, or 200 mg, or any other amount from about 0.1 mg to about 200 mg) of a compound of tetradecyl sulfate, a tetradecyl sulfate-like compound, or a pharmaceutically or cosmetically acceptable salt, solvate, prodrug, or ester thereof. The amount of active ingredient in the formulation can vary depending on the period of administration prescribed (including about 30 minutes, 1 hour, 6 hours, 12 hours, one day, 2 days, 3 days, 4 days, 5 days, 6 days, 7 days, 10 days, 2 weeks, 3 weeks, or any other time interval from about 5 minutes to about 1 month).

In certain embodiments is a formulation comprising, a compound of Formula I or Formula II, or a pharmaceutically or cosmetically acceptable salt, solvate, prodrug, or ester thereof wherein the injection volume is equal to about 2 mL. In certain embodiments is a formulation comprising, a compound of Formula I or Formula II, or a pharmaceutically or cosmetically acceptable salt, solvate, prodrug, or ester thereof wherein the injection volume is less than about 2 mL. In certain embodiments is a formulation comprising, a compound of Formula I or Formula II, or a pharmaceutically or cosmetically acceptable salt, solvate, prodrug, or ester thereof wherein the injection volume is equal to about 1.8 mL. In certain embodiments is a formulation comprising, a compound of Formula I or Formula II, or a pharmaceutically or cosmetically acceptable salt, solvate, prodrug, or ester thereof wherein the injection volume is less than about 1.8 mL. In certain embodiments is a formulation comprising, a compound of Formula I or Formula II, or a pharmaceutically or cosmetically acceptable salt, solvate, prodrug, or ester thereof wherein the injection volume is equal to about 1.6 mL. In certain embodiments is a formulation comprising, a compound of Formula I or Formula II, or a pharmaceutically or cosmetically acceptable salt, solvate, prodrug, or ester thereof wherein the injection volume is less than about 1.6 mL. In certain embodiments is a formulation comprising, a compound of Formula I or Formula II, or a pharmaceutically or cosmetically acceptable salt, solvate, prodrug, or ester thereof wherein the injection volume is equal to about 1.4 mL. In certain embodiments is a formulation comprising, a compound of Formula I or Formula II, or a pharmaceutically or cosmetically acceptable salt, solvate, prodrug, or ester thereof wherein the injection volume is less than about 1.4 mL. In certain embodiments is a formulation comprising, a compound of Formula I or Formula II, or a pharmaceutically or cosmetically acceptable salt, solvate, prodrug, or ester thereof wherein the injection volume is equal to about 1.2 mL. In certain embodiments is a formulation comprising, a compound of Formula I or Formula II, or a pharmaceutically or cosmetically acceptable salt, solvate, prodrug, or ester thereof wherein the injection volume is less than about 1.2 mL. In certain embodiments is a formulation comprising, a compound of Formula I or Formula II, or a pharmaceutically or cosmetically acceptable salt, solvate, prodrug, or ester thereof wherein the injection volume is equal to about 1 mL. In certain embodiments is a formulation comprising, a compound of Formula I or Formula II, or a pharmaceutically or cosmetically acceptable salt, solvate, prodrug, or ester thereof wherein the injection volume is less than about 1 mL. In certain embodiments is a formulation comprising, a compound of Formula I or Formula II, or a pharmaceutically or cosmetically acceptable salt, solvate, prodrug, or ester thereof wherein the injection volume is equal to about 0.8 mL. In certain embodiments is a formulation comprising, a compound of Formula I or Formula II, or a pharmaceutically or cosmetically acceptable salt, solvate, prodrug, or ester thereof wherein the injection volume is less than about 0.8 mL. In certain embodiments is a formulation comprising, a compound of Formula I or Formula II, or a pharmaceutically or cosmetically acceptable salt, solvate, prodrug, or ester thereof wherein the injection volume is equal to about 0.6 mL. In certain embodiments is a formulation comprising, a compound of Formula I or Formula II, or a pharmaceutically or cosmetically acceptable salt, solvate, prodrug, or ester thereof wherein the injection volume is less than about 0.6 mL. In certain embodiments is a formulation comprising, a compound of Formula I or Formula II, or a pharmaceutically or cosmetically acceptable salt, solvate, prodrug, or ester thereof wherein the injection volume is equal to about 0.4 mL. In certain embodiments is a formulation comprising, a compound of Formula I or Formula II, or a pharmaceutically or cosmetically acceptable salt, solvate, prodrug, or ester thereof wherein the injection volume is less than about 0.4 mL. In certain embodiments is a formulation comprising, a compound of Formula I or Formula II, or a pharmaceutically or cosmetically acceptable salt, solvate, prodrug, or ester thereof wherein the injection volume is equal to about 0.2 mL. In certain embodiments is a formulation comprising, a compound of Formula I or Formula II, or a pharmaceutically or cosmetically acceptable salt, solvate, prodrug, or ester thereof wherein the injection volume is less than about 0.2 mL. In certain embodiments is a formulation comprising, a compound of Formula I or Formula II, or a pharmaceutically or cosmetically acceptable salt, solvate, prodrug, or ester thereof wherein the injection volume is equal to about 0.1 mL. In certain embodiments is a formulation comprising, a compound of Formula I or Formula II, or a pharmaceutically or cosmetically acceptable salt, solvate, prodrug, or ester thereof wherein the injection volume is more than about 0.1 mL. In certain embodiments is a formulation comprising, a compound of Formula I or Formula II, or a pharmaceutically or cosmetically acceptable salt, solvate, prodrug, or ester thereof wherein the injection volume is equal to about 0.3 mL. In certain embodiments is a formulation comprising, a compound of Formula I or Formula II, or a pharmaceutically or cosmetically acceptable salt, solvate, prodrug, or ester thereof wherein the injection volume is more than about 0.3 mL. In certain embodiments is a formulation comprising, a compound of Formula I or Formula II, or a pharmaceutically or cosmetically acceptable salt, solvate, prodrug, or ester thereof wherein the injection volume is equal to about 0.5 mL. In certain embodiments is a formulation comprising, a compound of Formula I or Formula II, or a pharmaceutically or cosmetically acceptable salt, solvate, prodrug, or ester thereof wherein the injection volume is more than about 0.5 mL. In certain embodiments is a formulation comprising, a compound of Formula I or Formula II, or a pharmaceutically or cosmetically acceptable salt, solvate, prodrug, or ester thereof wherein the injection volume is equal to about 0.7 mL. In certain embodiments is a formulation comprising, a compound of Formula I or Formula II, or a pharmaceutically or cosmetically acceptable salt, solvate, prodrug, or ester thereof wherein the injection volume is more than about 0.7 mL. In certain embodiments is a formulation comprising, a compound of Formula I or Formula II, or a pharmaceutically or cosmetically acceptable salt, solvate, prodrug, or ester thereof wherein the injection volume is equal to about 0.9 mL. In certain embodiments is a formulation comprising, a compound of Formula I or Formula II, or a pharmaceutically or cosmetically acceptable salt, solvate, prodrug, or ester thereof wherein the injection volume is more than about 0.9 mL. In certain embodiments is a formulation comprising, a compound of Formula I or Formula II, or a pharmaceutically or cosmetically acceptable salt, solvate, prodrug, or ester thereof wherein the injection volume is more than about 1 mL. In certain embodiments is a formulation comprising, a compound of Formula I or Formula II, or a pharmaceutically or cosmetically acceptable salt, solvate, prodrug, or ester thereof wherein the injection volume is equal to about 1.1 mL. In certain embodiments is a formulation comprising, a compound of Formula I or Formula II, or a pharmaceutically or cosmetically acceptable salt, solvate, prodrug, or ester thereof wherein the injection volume is more than about 1.1 mL. In certain embodiments is a formulation comprising, a compound of Formula I or Formula II, or a pharmaceutically or cosmetically acceptable salt, solvate, prodrug, or ester thereof wherein the injection volume is equal to about 1.3 mL. In certain embodiments is a formulation comprising, a compound of Formula I or Formula II, or a pharmaceutically or cosmetically acceptable salt, solvate, prodrug, or ester thereof wherein the injection volume is more than about 1.3 mL. In certain embodiments is a formulation comprising, a compound of Formula I or Formula II, or a pharmaceutically or cosmetically acceptable salt, solvate, prodrug, or ester thereof wherein the injection volume is equal to about 1.5 mL. In certain embodiments is a formulation comprising, a compound of Formula I or Formula II, or a pharmaceutically or cosmetically acceptable salt, solvate, prodrug, or ester thereof wherein the injection volume is more than about 1.5 mL. In certain embodiments is a formulation comprising, a compound of Formula I or Formula II, or a pharmaceutically or cosmetically acceptable salt, solvate, prodrug, or ester thereof wherein the injection volume is equal to about 1.7 mL. In certain embodiments is a formulation comprising, a compound of Formula I or Formula II, or a pharmaceutically or cosmetically acceptable salt, solvate, prodrug, or ester thereof wherein the injection volume is more than about 1.7 mL. In certain embodiments is a formulation comprising, a compound of Formula I or Formula II, or a pharmaceutically or cosmetically acceptable salt, solvate, prodrug, or ester thereof wherein the injection volume is equal to about 1.9 mL. In certain embodiments is a formulation comprising, a compound of Formula I or Formula II, or a pharmaceutically or cosmetically acceptable salt, solvate, prodrug, or ester thereof wherein the injection volume is more than about 1.9 mL.

Provided herein are cosmetic and therapeutic methods comprising subcutaneously administering or providing to a human a formulation comprising a compound of Formula I or Formula II, or a pharmaceutically or cosmetically acceptable salt, solvate, prodrug, or ester thereof and a liquid carrier formulated for injection into a layer of subcutaneous fat for a human in need. In an embodiment, a formulation comprising tetradecyl sulfate of Formula II is administered to the human to treat an indication selected from one or more of: abdominal adiposity, regional adiposity, and exophthalmos due to thyroid eye disease. In certain embodiments, the formulation is provided to the human to affect a shape, contour, or appearance of the human body. In an embodiment, the shape, contour, or appearance is in a region of the body (e.g., the abdominal region or eye region of the human). In certain other embodiments, the formulation is administered or provided to the human subcutaneously as a periorbital, intraorbital, or submental injection. In an embodiment, a formulation described herein is administered or provided to the human subcutaneously to an abdominal region, an ophthalmic region, or a submental region. In certain embodiments of the cosmetic and/or therapeutic methods described herein, the formulation is administered or provided to the human in the inside region of the knees, the middle to upper area of the upper arm (including the tricep area), the submental area (including the area under the chin, for example the wattle (which is understood to refer to the fleshy fold of skin in the submental area of the human)), the abdomen, the hips, the inner thigh, the outer thigh, the buttocks, the lower back, the upper back, or the chest.

Provided herein is a method for treating a fat accumulation comprising administering an injectable formulation comprising a compound of Formula I or Formula II, or a pharmaceutically or cosmetically acceptable salt, solvate, prodrug, or ester thereof and a liquid carrier formulated for injection into a layer of subcutaneous fat for a human in need. In certain embodiments is a method for treating a fat accumulation comprising administering an injectable formulation comprising tetradecyl sulfate, a tetradecyl sulfate-like compound, or a pharmaceutically or cosmetically acceptable salt, solvate, prodrug, or ester thereof and a liquid carrier formulated for injection into a layer of subcutaneous fat for a human in need. Also provided are methods of treating regional adipose tissue comprising administering an injectable formulation comprising at least one compound of Formula I or Formula II or pharmaceutically or cosmetically acceptable salt, solvate, prodrug, or ester, or combinations thereof and a liquid carrier formulated for injection into a layer of subcutaneous fat for a human in need. Also provided are methods of treating regional adiposity comprising administering an injectable formulation comprising Formula II, or a pharmaceutically or cosmetically acceptable salt, solvate, prodrug, or ester thereof and a liquid carrier formulated for injection into a layer of subcutaneous fat for a human in need. Also provided are methods of treating regional adipose tissue comprising administering an injectable formulation comprising tetradecyl sulfate, a tetradecyl sulfate-like compound, or a pharmaceutically or cosmetically acceptable salt, solvate, prodrug, or ester thereof and a liquid carrier formulated for injection into a layer of subcutaneous fat for a human in need.

Provided herein is a method comprising administering an injectable formulation comprising at least one of a compound of Formula I or Formula II, or a pharmaceutically or cosmetically acceptable salt, solvate, prodrug, or ester, or combinations thereof and a liquid carrier formulated for injection into a layer of subcutaneous fat for a human in need, wherein administration results in lysing or destroying one or more adipose cells. In certain embodiments, the methods comprise administering an injectable formulation comprising tetradecyl sulfate of Formula II, or a pharmaceutically or cosmetically acceptable salt, solvate, prodrug, or ester thereof and a liquid carrier formulated for injection into a layer of subcutaneous fat for a human in need, wherein administration results in lysing or destroying one or more adipose cells. In certain embodiments, the methods described herein further result in an inflammatory reaction that at least partially removes or decreases destroyed or lysed adipose cells.

Provided herein is a method comprising administering an injectable formulation comprising a compound of Formula I or Formula II, or a pharmaceutically or cosmetically acceptable salt, solvate, prodrug, or ester thereof and a liquid carrier formulated for injection into a layer of subcutaneous fat for a human in need, wherein administration results in selectively lysing or destroying one or more adipose cells, leaving surrounding tissue largely unaffected.

Provided herein is a kit, comprising: a cosmetically or effective amount of a compound of Formula I or Formula II, or a pharmaceutically or cosmetically acceptable salt, solvate, prodrug, or ester thereof; an injector; and instructions for use. In certain embodiments of the kit, the tetradecyl sulfate or a pharmaceutically or cosmetically acceptable salt, solvate, prodrug, or ester thereof is in an aqueous form. In certain embodiments of the kit, the compound of Formula I or Formula II, or a pharmaceutically or cosmetically acceptable salt, solvate, prodrug, or ester thereof is in crystalline phase. In certain other embodiments, the compound of Formula I or Formula II, or a pharmaceutically or cosmetically acceptable salt, solvate, prodrug, or ester thereof is in an amorphous phase. In an embodiment, the compound of Formula I or Formula II, or a pharmaceutically or cosmetically acceptable salt, solvate, prodrug, or ester thereof is in a semi-crystalline phase. In certain embodiments of the kit, the compound of Formula I or Formula II, or a pharmaceutically or cosmetically acceptable salt, solvate, prodrug, or ester thereof is in a semi-amorphous phase. In some embodiments, a compound of Formula I or Formula II, or a pharmaceutically or cosmetically acceptable salt, solvate, prodrug, or ester thereof is in a crystalline or amorphous form. In some embodiments of the kit described herein, the compound of Formula II is sodium tetradecyl sulfate. In some embodiments, a formulation described herein comprises potassium tetradecyl sulfate. In certain embodiments of the kit, the injector contains a needle, is needleless, or comprises a subcutaneous applicator.

Provided herein is an injectable formulation for treating regional adipose tissue, regional adiposity, or regional fat accumulation comprising an effective amount of at least one compound of Formula I or Formula II, or a pharmaceutically or cosmetically acceptable salt, solvate, prodrug, or ester thereof; an effective amount of a glucocorticosteroid or a pharmaceutically or cosmetically acceptable salt, solvate, prodrug, or ester thereof; and a liquid carrier; wherein the compound of Formula I or Formula II, glucocorticosteroid, or salt, solvate, prodrug, or ester thereof and a liquid carrier are formulated for injection into a layer of subcutaneous fat for a human in need. In certain embodiments, the compound of Formula II is sodium tetradecyl sulfate. In some embodiments, the compound of Formula II is potassium tetradecyl sulfate. In certain embodiments, the glucocorticosteroid is selected from the group consisting of: dexamethasone, prednisolone, fluticasone, budesonide, and salts, solvates, prodrugs, or esters thereof. In certain embodiments, the carrier is a liquid carrier. In certain embodiments, the liquid carrier is a lipophilic liquid carrier. In an embodiment, the effective amount of tetradecyl sulfate is equal to or more than about 0.1% W/V to an amount that is equal to or less than about 10% W/V. In an embodiment, the effective amount of tetradecyl sulfate is less than about 1% W/V. In an embodiment, the effective amount of tetradecyl sulfate is about 1% W/V. In an embodiment, the effective amount of tetradecyl sulfate is greater than about 1% W/V. In an embodiment, the effective amount of tetradecyl sulfate is less than about 3% W/V. In an embodiment, the effective amount of tetradecyl sulfate is about 3% W/V. In an embodiment, the effective amount of tetradecyl sulfate is greater than about 3% W/V. In certain embodiments, the effective amount of the glucocorticosteroid is up to about 50 µg/day. In certain embodiments, the effective amount of the glucocorticosteroid is about 50 µg/day. In certain embodiments, the effective amount of the glucocorticosteroid is over about 50 µg/day. In an embodiment, a formulation described herein is an extended release formulation. In an embodiment, the formulation is a rapid-release formulation.

Provided herein is an injectable formulation for treating regional adipose tissue, regional adiposity, or regional fat accumulation comprising: an effective amount of at least one compound of Formula I or Formula II, or a pharmaceutically or cosmetically acceptable salt, solvate, prodrug, or ester thereof; an effective amount of deoxycholic acid or a pharmaceutically or cosmetically acceptable salt, solvate, prodrug, or ester thereof; and a liquid carrier wherein the tetradecyl sulfate, deoxycholic acid, and liquid carrier are formulated for injection into a layer of subcutaneous fat for a human in need. In certain embodiments, the compound of Formula II is sodium tetradecyl sulfate. In some embodiments, a formulation described herein comprises potassium tetradecyl sulfate.

Provided herein is a method of treating lipoma in an individual, comprising subcutaneously administering or providing to the individual a formulation described herein. In certain embodiments, the method of treating lipoma comprises administering to the individual an effective amount of a formulation comprising tetradecyl sulfate, a tetradecyl sulfate-like compound of Formula II, or a pharmaceutically or cosmetically acceptable salt, solvate, prodrug, or ester thereof; and a liquid carrier; wherein the tetradecyl sulfate or a pharmaceutically or cosmetically acceptable salt, solvate, prodrug, or ester thereof and a liquid carrier are formulated for injection into a layer of subcutaneous fat for a human in need thereof

DETAILED DESCRIPTION

Provided herein are pharmaceutical compositions, formulations, methods, and kits to achieve regional fat, adipose tissue, adipocyte and regional or localized adiposity reduction.

Provided herein, in certain embodiments, are injectable formulations for treating regional adipose tissue, regional adiposity, or regional fat accumulation. In certain embodiments, the formulations comprise an effective amount of at least one of a compound of Formula I or Formula II, or a pharmaceutically or cosmetically acceptable salt, solvate, prodrug, or ester thereof; and a liquid carrier; wherein the compound of Formula I or Formula II, or a pharmaceutically or cosmetically acceptable salt, solvate, prodrug, or ester thereof and a liquid carrier are formulated for injection into a layer of subcutaneous fat for a human in need thereof. In certain embodiments, the compound of Formula II is sodium tetradecyl sulfate. In some embodiments, the compound of Formula II is potassium tetradecyl sulfate. In certain embodiments, the formulation is an extended release formulation. In certain further embodiments, the formulation is a rapid-release formulation. In some embodiments, the therapeutically effective amount of tetradecyl sulfate is released for about 12 hours to about 45 days (e.g., about 3 days to about 10 days).

In some embodiments, are methods and formulations that facilitate dispersal of Formula I or Formula II, or a salt, solvate, prodrug, or ester thereof into a layer of subcutaneous fat at a regional fat site selected from one or more of the following: a submental region, an abdominal region, a waist, a hip, a lateral buttock, a thigh, a periorbital region, an intraorbital region, and intramuscular region. In certain embodiments is a formulation for the treatment at least one of: abdominal adiposity, regional adiposity, or exophthalmos caused by thyroid eye disease. In certain embodiments are formulations to affect a shape, contour, or appearance of the human body.

In some embodiments, are methods of treating regional adipose tissue, regional adiposity, or regional fat accumulation in an individual, comprising administering to the individual an effective amount of a formulation comprising: at least one of a compound of Formula I or Formula II, or a pharmaceutically or cosmetically acceptable salt, solvate, prodrug, or ester thereof and a liquid carrier; wherein the compound of Formula I or Formula II, or a pharmaceutically or cosmetically acceptable salt, solvate, prodrug, or ester thereof and a liquid carrier are formulated for injection into a layer of subcutaneous fat for a human in need thereof. In certain embodiments, the method of treating regional adipose tissue, regional adiposity, or regional fat accumulation further comprises administration of an effective amount of a glucocorticosteroid, or a pharmaceutically or cosmetically acceptable salt, solvate, prodrug, or ester thereof. In some embodiments, the method further comprises administration of an effective amount of deoxycholic acid, or a pharmaceutically or cosmetically acceptable salt, solvate, prodrug, or ester thereof.

Provided herein are methods of selective, ablative and/or non-ablative fat reduction for a human in need, comprising administering an effective amount of a formulation described herein. Also provided herein are methods of treating a lipoma in an individual, comprising subcutaneously administering or providing to the individual a formulation described herein.

In some embodiments are methods for increasing muscle mass in a human in need thereof, comprising administering a sustained release or rapid release formulation described herein.

In some embodiments, provided are one or more methods to reduce fat deposits under the eye, chin, or arm, as well as the buttock, calf, back, thigh, ankle, or stomach for a human in need thereof. In another embodiment, the methods described herein reduce specific types of fat deposits such as eyelid fat herniation, lipomas, lipodystrophy, buffalo hump lipodystrophy, or fat deposits associated with cellulite.

In some embodiments, is an injectable formulation for treating regional adipose tissue, regional adiposity, or regional fat accumulation comprising: an effective amount of Formula I or Formula II, or a pharmaceutically or cosmetically acceptable salt, solvate, prodrug, or ester thereof and a liquid carrier;

the compound of Formula I or Formula II, or a pharmaceutically or cosmetically acceptable salt, solvate, prodrug, or ester thereof and a liquid carrier formulated for injection into a layer of subcutaneous fat for a human in need. In select embodiments, the compound of Formula II is sodium tetradecyl sulfate. In some embodiments, the compound of Formula II is potassium tetradecyl sulfate. In certain embodiments, the formulation is stable for a period of at least 6 months at a temperature of about 0° C. to about 50° C. In some embodiments, the formulation allows dispersal of the tetradecyl sulfate or salt, solvate, prodrug, or ester thereof into the layer of subcutaneous fat at a regional fat site selected from one or more of the following: a submental region, an abdominal region, a waist, a hip, a lateral buttock, a thigh, a periorbital region, an intraorbital region, and intramuscular region. In some embodiments of the injectable formulations described herein, the carrier is a liquid carrier. In some embodiments of the injectable formulations described herein, the liquid carrier is a lipophilic liquid carrier. In an embodiment, tetradecyl sulfate, or a pharmaceutically or cosmetically acceptable salt, solvate, prodrug, or ester thereof is present in an amount that is equal to or more than about 0.2% W/V to an amount that is equal to or less than about 10% W/V. In certain embodiments is a formulation wherein the compound of Formula I or Formula II, or a pharmaceutically or cosmetically acceptable salt, solvate, prodrug, or ester thereof is present in an amount that is equal to or less than about 10% weight/volume (W/V). In certain embodiments, the compound of Formula I or Formula II, such as tetradecyl sulfate or a pharmaceutically or cosmetically acceptable salt, solvate, prodrug, or ester thereof is present in an amount that is equal to or more than about 0.1% W/V to an amount that is equal to or less than about 10% W/V. In another embodiment, the compound or a pharmaceutically or cosmetically acceptable salt, solvate, prodrug, or ester thereof is present in an amount that is equal to or more than about 0.2% W/V to an amount that is equal to or less than about 8% W/V. Also provided are embodiments of the formulations described herein wherein the compound of Formula I or Formula II, or a pharmaceutically or cosmetically acceptable salt, solvate, prodrug, or ester thereof is present in an amount that is equal to or more than about 0.3% W/V to an amount that is equal to or less than about 6% W/V. In an embodiment, a compound or a pharmaceutically or cosmetically acceptable salt, solvate, prodrug, or ester thereof is present in an amount that is equal to or more than about 0.4% W/V to an amount that is equal to or less than about 4% W/V. In some embodiments, a compound of Formula I or Formula II, or a pharmaceutically or cosmetically acceptable salt, solvate, prodrug, or ester thereof is present in an amount that is equal to or more than about 0.5% W/V to an amount that is equal to or less than about 3% W/V. In a further embodiment of the formulations described herein, a compound of Formula I or Formula II, or a pharmaceutically or cosmetically acceptable salt, solvate, prodrug, or ester thereof is present in an amount that is greater than 3% W/V. In a further embodiment of the formulations described herein, a compound of Formula I or Formula II, or a pharmaceutically or cosmetically acceptable salt, solvate, prodrug, or ester thereof is present in an amount that is equal to about 3% W/V. In a further embodiment of the formulations described herein, a compound of Formula I or Formula II, or a pharmaceutically or cosmetically acceptable salt, solvate, prodrug, or ester thereof is present in an amount that is less than 3% W/V. In a further embodiment of the formulations described herein, a compound of Formula I or Formula II, or a pharmaceutically or cosmetically acceptable salt, solvate, prodrug, or ester thereof is present in an amount that is greater than 1% W/V. In a further embodiment of the formulations wherein a compound of Formula I or Formula II, or a pharmaceutically or cosmetically acceptable salt, solvate, prodrug, or ester thereof is present in an amount that is equal to about 1% W/V. In a further embodiment of the formulations described herein, a compound of Formula I or Formula II, or a pharmaceutically or cosmetically acceptable salt, solvate, prodrug, or ester thereof is present in an amount that is less than 1% W/V. In an embodiment, a compound of Formula I or Formula II, or a pharmaceutically or cosmetically acceptable salt, solvate prodrug, or ester thereof is present in an amount that is equal to about 0.5% W/V. In certain embodiments, the compound of Formula II is tetradecyl sulfate, a tetradecyl sulfate-like compound, or a pharmaceutically or cosmetically acceptable salt, solvate, prodrug, or ester thereof.

In certain embodiments, the formulation also comprises administration of an effective amount of a glucocorticosteroid, or a pharmaceutically or cosmetically acceptable salt, solvate, prodrug, or ester thereof. In some embodiments, the glucocorticosteroid is selected from the group consisting of: dexamethasone, prednisolone, fluticasone, budesonide, and salts, solvates, prodrugs, or esters thereof In some embodiments, is a cosmetic or therapeutic method comprising subcutaneously administering or providing to a human a formulation for treating regional adipose tissue, regional adiposity, or regional fat accumulation comprising: an effective amount of a compound of Formula II, such as sodium tetradecyl sulfate, or a pharmaceutically or cosmetically acceptable salt, solvate, prodrug, or ester thereof; and a liquid carrier; the tetradecyl sulfate or a pharmaceutically or cosmetically acceptable salt, solvate, prodrug, or ester thereof and a liquid carrier formulated for injection into a layer of subcutaneous fat for a human in need. In an embodiment, provided is a method wherein the formulation described herein is administered to the human to treat an indication selected from one or more of: abdominal adiposity, regional adiposity, and exophthalmos due to thyroid eye disease. In some embodiments, provided is a cosmetic method wherein a formulation described herein is provided to the human to affect a shape, contour, or appearance of the human body. In certain embodiments, the shape, contour, or appearance is in a region of the body (e.g., the abdominal region or eye region of the human). In certain embodiments, a formulation described herein is administered or provided to the human subcutaneously as a periorbital, intraorbital, or submental injection. In an embodiment, a formulation described herein is administered or provided to the human subcutaneously to an abdominal region, an ophthalmic region, or a submental region. In certain embodiments, a formulation described herein is administered or provided to the human in the inside region of the knees, the middle to upper area of the upper arm (including the tricep area), the submental area (including the area under the chin, for example the wattle (which is understood to refer to the fleshy fold of skin in the submental area of the human)), the abdomen, the hips, the inner thigh, the outer thigh, the buttocks, the lower back, the upper back, or the chest.

In some embodiments, is a method for treating a fat accumulation comprising administering an injectable formulation described herein. In an embodiment, provided is a method for treating regional adipose tissue, comprising the step of administering an injectable formulation comprising at least one compound of Formula II described herein. In a certain embodiments, provided is a method for treating regional adiposity comprising administering an injectable formulation of tetradecyl sulfate described herein.

In some embodiments, is a method comprising administering an injectable formulation comprising a compound of Formula I or Formula II, or a pharmaceutically or cosmetically acceptable salt, solvate, prodrug, or ester thereof that results in lysing or destroying one or more adipose cells.

In some embodiments, is a method comprising administering an injectable formulation of tetradecyl sulfate, or a pharmaceutically or cosmetically acceptable salt, solvate, prodrug, or ester described herein, that results in selectively lysing or destroying one or more adipose cells while leaving surrounding tissue largely unaffected.

In some embodiments, is a kit, comprising: a cosmetically or therapeutically effective amount of at least one of a compound of Formula I or Formula II, or a pharmaceutically or cosmetically acceptable salt, solvate, prodrug, or ester thereof; an injector; and instructions for use. In certain embodiments, the kit comprises tetradecyl sulfate, or a pharmaceutically or cosmetically acceptable salt, solvate, prodrug, or ester thereof in an aqueous form. In some embodiments, the tetradecyl sulfate, or a pharmaceutically or cosmetically acceptable salt, solvate, prodrug, or ester thereof is in crystalline phase. In an embodiment, the tetradecyl sulfate or a pharmaceutically or cosmetically acceptable salt, solvate, prodrug, or ester thereof is in an amorphous phase. In a certain embodiment, the tetradecyl sulfate or a pharmaceutically or cosmetically acceptable salt, solvate, prodrug, or ester thereof is in a semi-crystalline phase. In certain embodiments, the tetradecyl sulfate or a pharmaceutically or cosmetically acceptable salt, solvate, prodrug, or ester thereof is in a semi-amorphous phase. In an embodiment, the tetradecyl sulfate or a pharmaceutically or cosmetically acceptable salt, solvate, prodrug, or ester thereof is in a crystalline or amorphous form. In certain embodiments of the kit, the injector contains a needle, is needleless, or comprises a subcutaneous applicator.

In some embodiments is a method of treating regional adipose tissue, regional adiposity, or regional fat accumulation in an individual, comprising administering to the individual an effective amount of a formulation comprising: a compound of Formula I or Formula II, or a pharmaceutically or cosmetically acceptable salt , solvate, prodrug, or ester thereof; and a liquid carrier; wherein the compound of Formula I or Formula II, or a pharmaceutically or cosmetically acceptable salt, solvate, prodrug, or ester thereof and a liquid carrier are formulated for injection into a layer of subcutaneous fat for a human in need thereof. In certain embodiments, the method also comprises administration of an effective amount of a glucocorticosteroid, or a pharmaceutically or cosmetically acceptable salt, solvate, prodrug, or ester thereof. In some embodiments, the glucocorticosteroid is selected from the group consisting of: dexamethasone, prednisolone, fluticasone, budesonide, and salts, solvates, prodrugs, or esters thereof.

In some embodiments, is a method of selective, ablative and/or non-ablative fat reduction in an individual in need, comprising: administering to said individual an effective amount of a formulation comprising a compound of Formula I or Formula II, or a pharmaceutically or cosmetically acceptable salt, solvate, prodrug, or ester thereof; and a liquid carrier; wherein the compound of Formula I or Formula II, or a pharmaceutically or cosmetically acceptable salt, solvate, prodrug, or ester thereof and a liquid carrier are formulated for injection into a layer of subcutaneous fat for a human in need. In certain embodiments, the method also comprises administering an effective amount of a glucocorticosteroid or a pharmaceutically or cosmetically acceptable salt, solvate, prodrug, or ester thereof. In some embodiments, the glucocorticosteroid is selected from the group consisting of: dexamethasone, prednisolone, fluticasone, budesonide, and salts, solvates, prodrugs, or esters thereof.

Provided herein in certain embodiments is an injectable formulation for treating regional adipose tissue, regional adiposity, or regional fat accumulation comprising: an effective amount of the compound of Formula I

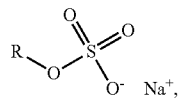

or a pharmaceutically or cosmetically acceptable salt, solvate, prodrug, or ester thereof; R is a saturated, linear $C_7$-$C_{24}$ hydrocarbon, or an unsaturated, linear $C_7$-$C_{24}$ hydrocarbon; and a liquid carrier; the compound of Formula I, or a pharmaceutically or cosmetically acceptable salt, solvate, prodrug, or ester thereof, and a liquid carrier formulated for injection into a layer of subcutaneous fat for a human in need. In certain embodiments, R is a saturated, linear $C_7$-$C_{24}$ hydrocarbon. In an embodiment, R is an unsaturated, linear $C_7$-$C_{24}$ hydrocarbon. In some embodiments, R is a saturated, linear $C_7$-$C_{12}$ hydrocarbon. In some embodiments, R is a saturated, linear $C_{12}$-$C_{18}$ hydrocarbon. In an embodiment, R is a saturated, linear $C_{18}$-$C_{24}$ hydrocarbon. In some embodiments, R is an unsaturated, linear $C_7$-$C_{12}$ hydrocarbon. In an embodiment, R is an unsaturated, linear $C_{12}$-$C_{18}$ hydrocarbon. In some embodiments, R is an unsaturated, linear $C_{18}$-$C_{24}$ hydrocarbon. In certain embodiments, the unsaturated, linear hydrocarbon comprises at least one alkene moiety. In some embodiments, the unsaturated, linear hydrocarbon comprises at least one alkene moiety of cis configuration. In certain embodiments, the unsaturated, linear hydrocarbon comprises at least one alkene moiety of trans configuration. In some embodiments, the unsaturated, linear hydrocarbon comprises at least one alkyne moiety.

In certain embodiments, the injectable formulation provided herein for treating regional adipose tissue, regional adiposity, or regional fat accumulation comprise an effective amount of the compound of Formula I

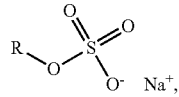

wherein R is a saturated or unsaturated, linear $C_{14}$ hydrocarbon. In certain embodiments, the unsaturated, linear hydrocarbon comprises at least one alkene moiety. In some embodiments, the unsaturated, linear hydrocarbon comprises at least one alkene moiety of cis configuration. In some embodiments, the unsaturated, linear hydrocarbon comprises at least one alkene moiety of trans configuration. In certain embodiments, the unsaturated, linear hydrocarbon comprises at least one alkyne moiety.

Sodium Tetradecyl Sulfate:

Sodium tetradecyl sulfate is a non-ionic detergent, consisting of two components: a polar hydrophilic (dodecyl alcohol) and an apolar hydrophobic (polyethylene oxide) chain. Provided below is the chemical structure of sodium tetradecyl sulfate and sodium tetradecyl sulfate-like compounds.

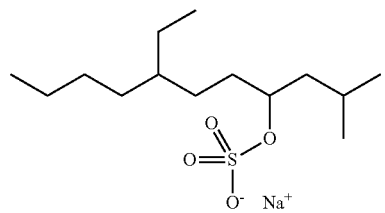 [SMILES: CCCCC(CC)CCC(CC(C)C)OS(=O)(=O)[O-] ; [Na+]]

In certain embodiments the formulations described herein comprises sodium tetradecyl sulfate or a sodium tetradecyl sulfate-like compound.

While not wishing to be bound by theory, sodium tetradecyl sulfate and related compounds may preferentially lyse fat cells while leaving surrounding tissue largely unaffected. Accordingly, in some embodiments, the methods described herein provide selective reduction of regional and/or subcutaneous accumulations of adipose tissue and adipocytes, including cellulite, through subcutaneous administration of sodium tetradecyl sulfate, or sodium tetradecyl sulfate-like compounds. In some embodiments, the compositions described herein are useful for treating cellulitic fat accumulation and/or lipomas.

In certain embodiments, are formulations for treating regional adipose tissue, regional adiposity, or regional fat accumulation. In certain embodiments, the formulations comprise an effective amount of at least one compound of Formula I or Formula II, or a pharmaceutically or cosmetically acceptable salt, solvate, prodrug, or ester thereof; and a liquid carrier; wherein the compound of Formula I or Formula II, or a pharmaceutically or cosmetically acceptable salt, solvate, prodrug, or ester thereof and a liquid carrier formulated for injection into a layer of subcutaneous fat for a human in need thereof. In certain embodiments, the compound of Formula II is sodium tetradecyl sulfate. In certain embodiments, the compound of Formula II is potassium tetradecyl sulfate. In some embodiments, the formulation is stable for a period of at least 6 months at a temperature of about 0° C. to about 50° C. In certain embodiments, the tetradecyl sulfate, or a pharmaceutically or cosmetically acceptable salt, solvate, prodrug, or ester thereof is present in an amount that is equal to or less than about 10% weight/volume (W/V). In certain embodiments the tetradecyl sulfate or a pharmaceutically or cosmetically acceptable salt, solvate, prodrug, or ester thereof is present in an amount that is equal to or more than about 0.1% W/V to an amount that is equal to or less than about 10% W/V. In some other embodiments the tetradecyl sulfate, or a pharmaceutically or cosmetically acceptable salt, solvate, prodrug, or ester thereof is present in an amount that is equal to or more than about 0.2% W/V to an amount that is equal to or less than about 8% W/V. In certain embodiments, the tetradecyl sulfate, or a pharmaceutically or cosmetically acceptable salt, solvate, prodrug, or ester thereof is present in an amount that is equal to or more than about 0.3% W/V to an amount that is equal to or less than about 6% W/V. In some other embodiments the tetradecyl sulfate, or a pharmaceutically or cosmetically acceptable salt, solvate, prodrug, or ester thereof is present in an amount that is equal to or more than about 0.4% W/V to an amount that is equal to or less than about 4% W/V. In select embodiments, the tetradecyl sulfate, or a pharmaceutically or cosmetically acceptable salt, solvate, prodrug, or ester thereof is present in an amount that is equal to or more than about 0.5% W/V to an amount that is equal to or less than about 3% W/V. In some other embodiments the tetradecyl sulfate, or a pharmaceutically or cosmetically acceptable salt, solvate, prodrug, or ester thereof is present in an amount that is less than about 3% W/V. In some other embodiments the tetradecyl sulfate, or a pharmaceutically or cosmetically acceptable salt, solvate, prodrug, or ester thereof is present in an amount that is equal to about 3% W/V. In some other embodiments the tetradecyl sulfate, or a pharmaceutically or cosmetically acceptable salt, solvate, prodrug, or ester thereof is present in an amount that is greater than about 3% W/V. In some other embodiments the tetradecyl sulfate, or a pharmaceutically or cosmetically acceptable salt, solvate, prodrug, or ester thereof is present in an amount that is less than about 1% W/V. In some other embodiments the tetradecyl sulfate, or a pharmaceutically or cosmetically acceptable salt, solvate, prodrug, or ester thereof is present in an amount that is equal to about 1% W/V. In some other embodiments the tetradecyl sulfate, or a pharmaceutically or cosmetically acceptable salt, solvate, prodrug, or ester thereof is present in an amount that is greater than about 1% W/V. In certain further embodiments, the tetradecyl sulfate, or a pharmaceutically or cosmetically acceptable salt, solvate, prodrug, or ester thereof is present in an amount that is equal to about 0.5% W/V.

In certain embodiments, the formulation also comprises an alcohol having 3 to 7 carbon atoms. In certain embodiments, the alcohol having 3 to 7 carbon atoms is present in an amount less than about 10% w/v. In certain embodiments, the alcohol having 3 to 7 carbon atoms is present in an amount less than about 8% w/v. In certain embodiments, the alcohol having 3 to 7 carbon atoms is present in an amount less than about 6% w/v. In certain embodiments, the alcohol having 3 to 7 carbon atoms is present in an amount less than about 4% w/v. In certain embodiments, the alcohol having 3 to 7 carbon atoms is present in an amount less than about 2% w/v. In certain embodiments, the alcohol having 3 to 7 carbon atoms is present in an amount between 0.5% w/v and about 10% w/v. In certain embodiments, the alcohol having 3 to 7 carbon atoms is present in an amount between 1% w/v and about 7% w/v. In certain embodiments, the alcohol having 3 to 7 carbon atoms is present in an amount between 1% w/v and about 5% w/v. In certain embodiments, the alcohol having 3 to 7 carbon atoms is present in an amount between 1% w/v and about 3% w/v. In certain embodiments, the alcohol having 3 to 7 carbon atoms is present in an amount of approximately 2% w/v. In certain embodiments, the alcohol having 3 to 7 carbon atoms is propylene glycol. In certain embodiments, the alcohol having 3 to 7 carbon atoms is polyethylene glycol. In certain embodiments, the alcohol having 3 to 7 carbon atoms is benzyl alcohol.

In certain embodiments, the phrase "pharmaceutically acceptable salt(s)" means those salts of compounds described herein that are safe and effective for administration in mammals. Pharmaceutically acceptable salts include salts of acidic or basic groups present in compounds described herein. In certain embodiments, the pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. In certain embodiments, one or more compounds described herein form pharmaceutically acceptable salts with various amino acids. In certain embodiments, the base salts include, but are not limited to, aluminum, calcium, lithium, magnesium, potassium, sodium, zinc, and diethanolamine salts. Pharmaceutically acceptable salts in certain embodiments of the formulations described herein, are as described in BERGE ET AL., 66 J. PHARM. SCI. 1-19 (1977), incorporated in entirety by reference herein.

In certain embodiments, the term "cosmetically acceptable salt" means any salt that is cosmetically tolerated if used appropriately for a cosmetic treatment especially if used on or applied to humans and/or mammals. In certain embodiments, these salts include, but are not restricted to the salts used to form base addition salts, either inorganic, such as for example and in a non-limiting sense, lithium, sodium, potassium, calcium, magnesium or aluminum, among others, or organic such as for example and in a non-limiting sense, ethylamine, diethylamine, ethylenediamine, ethanolamine, diethanolamine, arginine, lysine, histidine, or piperazine among others; or acid addition salts, either organic, such as for example and in a non-limiting sense, acetate, citrate, lactate, malonate, maleate, tartrate, fumarate, benzoate, aspartate, glutamate, succinate, oleate, trifluoroacetate, oxalate, pamoate or gluconate among others, or inorganic, such as for example and in a non-limiting sense, chloride, sulfate, borate, or carbonate among others. The cosmetically acceptable salts described herein can be obtained by conventional methods well known in the state of the art as described in BERGE ET AL., 66 J. PHARM. SCI. 1-19 (1977), incorporated in entirety by reference herein.

In some embodiments, the formulations described herein are injectable by means of subcutaneous injection. Subcutaneous administration has the benefit of local, targeted administration. Unlike other systemic modes of administration, subcutaneous administration results in a localized distribution of the active agents. In certain embodiments, these injectable formulations comprise a compound of Formula I or Formula II, or a pharmaceutically or cosmetically acceptable salt, solvate, prodrug, or ester thereof in an injection volume that is equal to or less than about 2 mL. In some other embodiments the compound of Formula I or Formula II, or a pharmaceutically or cosmetically acceptable salt, solvate, prodrug, or ester thereof injection volume is equal to or more than about 0.05 mL to an injection volume that is equal to or less than about 2 mL. In certain other embodiments, the compound of Formula I or Formula II, or a pharmaceutically or cosmetically acceptable salt, solvate, prodrug, or ester thereof injection volume is equal to or more than about 0.1 mL to an injection volume that is equal to or less than about 1.8 mL. In some embodiments, the compound of Formula I or Formula II, or a pharmaceutically or cosmetically acceptable salt, solvate, prodrug, or ester thereof injection volume is equal to or more than about 0.2 mL to an injection volume that is equal to or less than about 1.6 mL. In certain embodiments, the compound of Formula I or Formula II, or a pharmaceutically or cosmetically acceptable salt, solvate, prodrug, or ester thereof injection volume is equal to or more than about 0.3 mL to an injection volume that is equal to or less than about 1.4 mL. In select embodiments, the compound of Formula I or Formula II, or a pharmaceutically or cosmetically acceptable salt, solvate, prodrug, or ester thereof injection volume is equal to or more than about 0.4 mL to an injection volume that is equal to or less than about 1.2 mL. In some embodiments, the compound of Formula I or Formula II, or a pharmaceutically or cosmetically acceptable salt, solvate, prodrug, or ester thereof injection volume is equal to or more than about 0.5 mL to an injection volume that is equal to or less than about 1 mL. In some embodiments, a compound of Formula I or Formula II, or a pharmaceutically or cosmetically acceptable salt, solvate, prodrug, or ester thereof injection volume is equal to about 0.1 mL. In some further embodiments is provided a compound of Formula I or Formula II, or a pharmaceutically or cosmetically acceptable salt, solvate, prodrug, or ester thereof injection volume is equal to about 0.2 mL. In certain embodiments, a compound of Formula I or Formula II, or a pharmaceutically or cosmetically acceptable salt, solvate, prodrug, or ester thereof injection volume is equal to about 0.5 mL. In select embodiments, a compound of Formula I or Formula II, or a pharmaceutically or cosmetically acceptable salt, solvate, prodrug, or ester thereof injection volume is equal to about 1 mL. In certain embodiments, a compound of Formula I or Formula II, or a pharmaceutically or cosmetically acceptable salt, solvate, prodrug, or ester thereof injection volume is equal to about 2 mL.

In certain embodiments, the formulations described herein are administered to an individual to treat an indication selected from one or more of: abdominal adiposity, regional adiposity, and exophthalmos due to thyroid eye disease. In certain embodiments are provided formulations to affect a shape, contour, or appearance of the human body. In some embodiments are provided cosmetic methods and formulations wherein the formulation is administered or provided to the human subcutaneously as a periorbital, intraorbital, or submental injection. In certain embodiments, the formulations described herein are administered or provided to the individual subcutaneously to an abdominal region, an ophthalmic region, or a submental region.

Multiple injections over a region are applied to achieve a cosmetic effect. These injections may be spaced from 0.1 to up to 5 cm apart. A small volume per injection, less than 0.5 ml, may require spacing 1.0 cm or less, with larger volumes per injection allowing for larger spacing, such that 1.0 ml to 2.0 ml per injection may allow spacing of 1 cm or more and reduce the number of injections required to treat an area. Improving the cosmetic effect and reducing side effects may also be achieve by using larger per injection volume and a lower concentration (w/v) of tetradecyl sulfate, a tetradecyl sulfate-like compound or a cosmetically acceptable salt, solvate, prodrug, or ester. A 0.1-1.0% (w/v) with a 1 ml to per injection volume may provide the desired cosmetic effect with fewer side effects.

More than one treatment session of a certain region spaced 1-8 weeks apart may be required to achieve the desired cosmetic effect. In one treatment embodiment, five to twenty 0.1 to 1.0 ml injections spaced 0.1 cm to 1.0 cm apart of 0.1% to 1.0% weight/volume of tetradecyl sulfate, a tetradecyl sulfate-like, or cosmetically acceptable salts, solvates, prodrugs, or esters thereof, are injected into the submental (under chin) region of a patient. The treatment is repeated up to 6 times at two to four week intervals until the desired cosmetic effect is achieved. In another treatment embodiment, ten 0.2 ml injections spaced 0.5 cm apart of 0.5% weight/volume of tetradecyl sulfate, a tetradecyl sulfate-like compound, or a cosmetically acceptable salt, solvate, prodrug, or ester thereof, are injected into the submental (under chin) region of a patient. The treatment is repeated 4 times at 4 week intervals until the desired cosmetic effect is achieved. In another treatment embodiment, ten 0.2 ml injections spaced 1.0 cm apart of 1.0% weight/volume of tetradecyl sulfate, a tetradecyl sulfate like compound, or a cosmetically acceptable salt, solvate, prodrug, or ester thereof, are injected into the submental (under chin) region of a patient. The treatment is repeated 4 times at 4 week intervals until the desired cosmetic effect is achieved. In still another treatment embodiment, ten 0.4 ml injections spaced 1.0 cm apart of 0.5% weight/volume of tetradecyl sulfate, a tetradecyl sulfate-like compound, or a cosmetically acceptable salt, solvate, prodrug, or ester thereof, are injected into the submental (under chin) region of a patient. The treatment is repeated 4 times at 4 week intervals until the desired cosmetic effect is achieved. In another treatment embodiment, up to twenty 0.2 ml injections spaced 1.0 cm apart of 1.0% weight/volume of tetradecyl sulfate, a tetradecyl sulfate like compound, or a cosmetically acceptable salt, solvate, prodrug, or ester thereof, are injected into the submental (under chin) region of a patient. The treatment is repeated up to 4 times at 4-week intervals until the desired cosmetic effect is achieved. In another still another treatment embodiment, up to twenty 0.2 ml injections spaced 1.0 cm apart of 0.5% weight/volume of tetradecyl sulfate, a tetradecyl sulfate-like compound, or a cosmetically acceptable salt, solvate, prodrug, or ester thereof, are injected into the submental (under chin) region of a patient. The treatment is repeated 4 times at 4 week intervals until the desired cosmetic effect is achieved.

In certain embodiments, the formulations described herein are administered or provided to the individual in the inside region of the knees, the middle to upper area of the upper arm (including the tricep area), the submental area (including the area under the chin, for example the wattle (which is understood to refer to the fleshy fold of skin in the submental area of the human)), the abdomen, the hips, the inner thigh, the outer thigh, the buttocks, the lower back, the upper back, or the chest.

In certain embodiments, the formulation comprising a compound of Formula I or Formula II, such as sodium tetradecyl sulfate, further comprises a glucocorticosteroid, or a pharmaceutically or cosmetically acceptable salt, solvate, prodrug, or ester thereof. Some embodiments also comprise a bile acid such as deoxycholic acid, or a pharmaceutically or cosmetically acceptable salt, solvate, prodrug, or ester thereof. In certain embodiments, the formulation is an extended release formulation. In certain other embodiments, the formulation is a rapid-release formulation. In some embodiments, the therapeutically effective amount of the tetradecyl sulfate is released for about 12 hours to about 45 days (e.g., about 3 days to about 10 days).

In some embodiments are methods and formulations that facilitate dispersal of tetradecyl sulfate, a tetradecyl sulfate-like compound of Formula II, or salt, solvate, prodrug, or ester thereof into a layer of subcutaneous fat at a regional fat site selected from one or more of the following: a submental region, an abdominal region, a waist, a hip, a lateral buttock, a thigh, a periorbital region, an intraorbital region, and intramuscular region. In certain embodiments is a formulation for the treatment of at least one of: abdominal adiposity, regional adiposity, or exophthalmos caused by thyroid eye disease. In certain embodiments are formulations that affect a shape, contour, or appearance of the human body.

In certain embodiments, provided herein are kits, comprising: a cosmetically or therapeutically effective amount of tetradecyl sulfate, a tetradecyl sulfate-like compound, or a pharmaceutically or cosmetically acceptable salt, solvate, prodrug, or ester thereof; an injector; and instructions for use.

In some embodiments, is a method of treating regional adipose tissue, regional adiposity, or regional fat accumulation in an individual, comprising administering to the individual an effective amount of a formulation comprising: at least one of a compound of Formula I or Formula II, or a pharmaceutically or cosmetically acceptable salt, solvate, prodrug, or ester thereof; and a liquid carrier; wherein the compound of Formula I or Formula II, or a pharmaceutically or cosmetically acceptable salt, solvate, prodrug, or ester thereof and a liquid carrier are formulated for injection into a layer of subcutaneous fat for a human in need thereof. In certain embodiments, provided is a method of treating regional adipose tissue, regional adiposity, or regional fat accumulation that comprises administration of an effective amount of a glucocorticosteroid or a pharmaceutically or cosmetically acceptable salt, solvate, prodrug, or ester thereof. In some embodiments, the method further comprises administration of an effective amount of deoxycholic acid or a pharmaceutically or cosmetically acceptable salt, solvate, prodrug, or ester thereof Provided herein are methods of selective, ablative and/or non-ablative fat reduction for a human in need, comprising: administering an effective amount of a formulation described herein. Also provided herein are methods of treating a lipoma in an individual, comprising subcutaneously administering or providing to the individual a formulation described herein.

In some embodiments is a method for increasing muscle mass in a human in need thereof, comprising administering a sustained release or rapid release formulation described herein.

In some embodiments, are one or more methods to reduce fat deposits under the eye, chin, or arm, as well as the buttock, calf, back, thigh, ankle, or stomach. In another embodiment, the methods reduce specific types of fat deposits such as eyelid fat herniation, lipomas, lipodystrophy, buffalo hump lipodystrophy, or fat deposits associated with cellulite As used herein, the term "tetradecyl sulfate-like compound" refers to a compound of Formula I or Formula II, or salts, solvates, prodrugs, or esters thereof As used herein, the term "coadministered," refers to the administration of two or more therapeutic agents in a single formulation or separate formulations or routes of administration in any order for the purpose of treating the same health condition (e.g., a lipoma) in the same subject.

A "therapeutically effective amount," as used herein, refers to a sufficient amount of an agent (e.g., sodium tetradecyl sulfate) or other compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case can be determined using techniques, such as a dose escalation study. The term "therapeutically effective amount" includes, for example, a prophylactically effective amount. An "effective amount" of a compound disclosed herein, is an amount effective to achieve a desired pharmacologic effect or therapeutic improvement without undue adverse side effects. It is to be understood that "an effect amount" or "a therapeutically effective amount" can vary from subject to subject, due to variation in metabolism of the compound of Formula I or Formula II, age, weight, general condition of the subject, the condition being treated, the severity of the condition being treated, and the judgment of the prescribing physician.

A "cosmetically effective amount" as used herein refers to the amount of a compound sufficient to improve the outward physical appearance of a subject. The outward physical appearance of a subject includes, for example, the reduction of fat deposition in certain regions of the body including, for example, the midsection of the body. "Cosmetically effective" as used herein, also refers to a sufficient amount of an agent (e.g., sodium tetradecyl sulfate) which will improve the cosmetic appearance at the localized site of treatment. A "cosmetically effective" amount of tetradecyl sulfate is an amount effective to achieve a cosmetically desirable improvement. It is to be understood that a "cosmetically effective" amount can vary from subject to subject, due to numerous factors including age, weight, general condition of the subject, the condition being treated, the severity of the condition being treated, and the judgment of the prescribing physician.

Bile Acid

Bile acids are steroid acids found predominantly in the bile of mammals. Bile acids are made in the liver by the cytochrome P450-mediated oxidation of cholesterol. They are conjugated with taurine or the amino acid glycine, or with a sulfate or a glucuronide, and are then stored in the gallbladder, which concentrates the salts by removing the water. In humans, the rate limiting step is the addition of a hydroxyl group on position 7 of the steroid nucleus by the enzyme cholesterol-7-alpha-hydroxylase. Upon eating a meal, the contents of the gallbladder are secreted into the intestine, where bile acids serve the purpose of emulsifying dietary fats. Bile acids serve other functions, including eliminating cholesterol from the body, driving the flow of bile to eliminate catabolites from the liver, emulsifying lipids and fat soluble vitamins in the intestine to form micelles that can be transported via the lacteal system, and aiding in the reduction of the bacteria flora found in the small intestine and biliary tract.

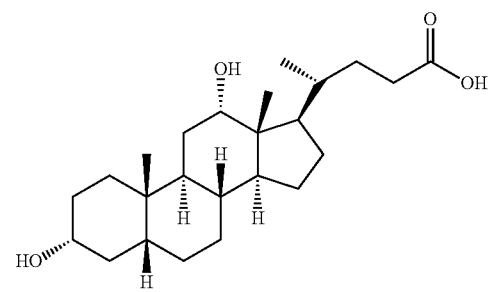

Formula XVIII

In humans, the most important bile acids are cholic acid, deoxycholic acid, and chenodeoxycholic acid. Deoxycholic acid is one of the secondary bile acids, which are metabolic byproducts of intestinal bacteria. The two primary bile acids secreted by the liver are cholic acid and chenodeoxycholic acid. Bacteria metabolize chenodeoxycholic acid into the secondary bile acid lithocholic acid, and they metabolize cholic acid into deoxycholic acid. Additional secondary bile acids include ursodeoxycholic acid. In the human body deoxycholic acid of Formula XVIII is used in the emulsification of fats for the absorption in the intestine.

In some embodiments, one or more of deoxycholic acid, cholic acid, chenodeoxycholic acid, and sodium deoxycholate is co-administered with a formulation described herein and the effective amount of sodium deoxycholate is about 0.01 to about 100 mg/day, e.g., about 1 mg/day to about 50 mg/day, about 0.01 mg/day to about 0.1 mg/day, about 0.05 mg/day to about 0.5 µg/day, about 50 mg/day to about 100 mg/day, about 5 mg/day to about 45 mg/day, about 0.75 mg/day to about 75 mg/day, about 25 mg/day to about 50 mg/day of bile acid, or any other dose of bile acid from about 0.01 mg/day to about 100 mg/day.

In some embodiments, in addition to treating a human with any of the compositions described herein, a physician or other authorized medical caregiver prescribes a liposuction procedure, or performs a liposuction procedure on the human to further reduce regional fat deposits.

In some embodiments, a liposuction procedure is performed on a human who has been administered a composition comprising a therapeutically effective amount of a compound of Formula I or Formula II, or a pharmaceutically or cosmetically acceptable salt, solvate, prodrug, or ester thereof. Without wishing to be bound by theory, administering any of the just-described sustained release pharmaceutical compositions to a subject prior to liposuction is likely to increase the efficacy of the liposuction procedure.

Embodiments of the composition are formulated for administration by any suitable method, for example, as described in *Remington: The Science And Practice Of Pharmacy* (21st ed., Lippincott Williams & Wilkins) Exemplary routes of administration include, but are not limited to parenteral, oral, subcutaneous, topical, intramuscular, transdermal, transmucosal, sublingual, intranasal, transvascular, subcutaneous, orbital, or respiratory. In some embodiments, the composition is formulated for injection of an area at which treatment is desired, for example, in a regional fat deposit.

Any suitable pharmaceutically acceptable excipient appropriate for a particular route of administration can be used. In some embodiments, the pharmaceutically acceptable excipient is disodium phosphate. In some embodiments, the pharmaceutically acceptable excipient is dihydrogen phosphate. In some embodiments, the pharmaceutically acceptable excipient is sodium hydroxide. The formulation may also contain any suitable pharmaceutically acceptable carrier. Examples of pharmaceutically acceptable carriers include, but are not limited to, buffers, saline, or other aqueous media. In certain embodiments, the formulation has a pH of from about 6 to 10. In some embodiments, the formulation has a pH of about 7 to 8. The compounds of the invention are preferably soluble in the carrier which is employed for their administration (e.g., subcutaneous). Alternatively, a suspension of the active compound or compounds (e.g., a suspension of crystalline microparticles) in a suitable carrier is employed. Some embodiments comprise any suitable lipophilic carrier, for example, modified oils (e.g., Cremophor® BASF, Germany), soybean oil, propylene glycol, polyethylene glycol, derivatized polyethers, combinations thereof, and the like. Some embodiments comprise a microparticulate and/or nanoparticulate carrier for at least one of the beta-2 receptor agonists and/or glucocorticosteroids, as discussed in greater detail below. Some embodiments comprise one or more sustained or controlled release carriers or agents, for example, polymer microspheres. Some embodiments comprise excipients suitable for stable suspensions for micronized particles of tetradecyl sulfate.

Injectable formulations are administered using any method known in the art, for example, using a single needle, multiple needles, and/or using a needleless injection device. In some embodiments, a tissue loading dose of the active ingredients formulated in a suitable carrier delivered by injection. In some embodiments, delivery comprises single needle injection. In some embodiments, delivery comprises injection using a multi-needle array, which, in some embodiments, provides a wide dispersion of the formulation in the target tissue. In some embodiments, formulations are injected in a manner that allows dispersal into the appropriate layer of subcutaneous fat in areas where regional fat.

The interval between administration of the compound of Formula I or Formula II, glucocorticosteroid, and/or bile acid can be an interval from about 5 minutes to about 1 month, e.g., 30 minutes, 1 hour, 6 hours, 12 hours, one day, 2 day, 3 days, 4 days, 5 days, 6 days, 7 days, 10 days, 2 weeks, 3 weeks, or any other time interval from about 5 minutes to about 1 month.

Some embodiments of the formulations described herein comprise one or more sustained or controlled release agents for providing a sustained or controlled release of a compound of Formula II, a glucocorticosteroid, and deoxycholic acid or pharmaceutical or cosmetically acceptable salts, solvates, prodrugs, or esters thereof. In some embodiments formulations comprise the compound of Formula II, and at least one of beta-2 agonist, glucocorticosteroid, and deoxycholic acid. In some embodiments, biocompatible, biodegradable, sustained, or controlled release formulations provide local tissue activity. Sustained release can be over a period from about 12 hours to about 12 months, e.g., one day, 3 days, 7 days, 10 days, 1 month, 45 days, 2 months, 3 months, 4 months, 6 months, 8 months, 9 months, 10 months, 11 months, or any other time period from about 12 hours to about 12 months. Suitable sustained or controlled release agents or carriers include polymers, macromolecules, active ingredient conjugates, hydrogels, contaminations thereof, and the like. Some embodiments of the sustained release carrier target fat, for example, liposomes. Preferably, the sustained release materials are selected to facilitate delivery of a substantially equal amount of the active substance per unit time. Several rounds of injections of the sustained release formulation can be made over time to treat a single area. In some embodiments, sustained release results from formulating the compound of Formula II, as a suspension of crystalline drug microparticles.

In some embodiments, the sustained release agent comprises a polymer, for example, polylactides, polyglycolides, poly(lactide glycolides) polylactic acids, polyglycolic acids, polyanhydrides, polyorthoesters, polyetheresters, polycaprolactones, polyesteramides, polycarbonates, polycyanoacrylates, polyurethanes, polyacrylates, and blends, mixtures, or copolymers of the above, which are used to encapsulate, bind, or conjugate with the active ingredients(s) (e.g., beta adrenergic agonists and/or glucocorticosteroids). Some preferred embodiments of sustained release polymers comprise polyethylene glycol groups to which one or more of the active ingredients are conjugated. In some preferred embodiments, the sustained release agent comprises poly (lactide glycolide) (PLGA, poly(lactic-co-glycolic acid)) copolymer of Formula XIX.

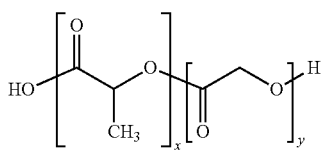

Formula XIX

Some embodiments of the sustained release agent comprise one or more hydrogels, including modified alginates. Examples of suitable modified alginates include those disclosed in WO 98/12228 which is incorporated by reference for purposes of that disclosure. Some embodiments of the sustained release agent comprise an albumin-based nanoparticle carrier or excipient.

In some embodiments, a formulation comprising a prepolymer solution is injected into the target tissue site, where it is then polymerized (e.g., by photopolymerization) or solidified (e.g., by using temperature sensitive gelling materials) in vivo.

In some embodiments, the controlled release materials have release characteristics designed for the particular application of tissue reduction. In some embodiments, the sustained release or controlled release agent is formed into microparticles, such as microspheres, which are formulated as an injectable solution and/or gel. In some embodiments, the microparticles range in size from about 10 µm to about 100 µm in diameter (e.g., about 15 µm, 20 µm, 25 µm, 30 µm, 40 µm, 50 µm, 60 µm, 70 µm, 80 µm, 90 µm or any other diameter from about 10 µm to about 100 µm). In some embodiments, the microparticles are uniform in size. In other embodiments, the microparticles vary in size by about 10% to about 300%, e.g., 30%, 40%, 50%, 70%, 80%, 90%, 120%, 150%, 170%, 190%, 200%, 225%, 250%, 275%, or by any other percentage variation in size from about 10% to about 300%. In some embodiments, formulations comprising alginates and/or poly(lactide-co-glycolide)s of Formula XIX are provided as an injectable gel or processed into microspheres. In other embodiments, the beta-2 agonist or a corticosteroid (or other compounds for reducing beta adrenergic receptor desensitization) are formed as crystalline microparticles. Other examples of suitable injectable biodegradable, biocompatible materials suitable for microparticle formation include chitosan, dextran, hydroxyapatite, and silicon.

Microspheres and/or microparticles are formed using any method, including by solvate evaporation and/or emulsion polymerization. In some embodiments, the microspheres have average diameters of from about 5 µm to about 60 µm, preferably, about 20 µm. In some embodiments, PLGA is manufactured with varying ratios of lactide to glycolide depending on the desired rate of release of the active ingredient(s). Because the rate of degradation of this copolymer is proportional to its crystallinity and the proportion of glycolide in the formulation, non-racemic mixtures of the lactide and/or glycolide increase crystallinity and slow the rate of degradation. Higher proportions of glycolide increase the rate of degradation. In some embodiments, a ratio of about 65%-75% lactide to about 25%-35% glycolide provides active ingredients released over from about 2 weeks to about 45 days. In other embodiments, the ratio of lactide to glycolide is from about 0:100 to about 100:0, thereby providing other release rates.

Some embodiments of the microspheres or microparticles comprise hollow and/or porous interiors. In some embodiments, the microspheres comprise a solid or porous outer shell.

The microspheres comprising the active ingredient(s) are suspended in about 10 ml to about 20 ml of an appropriate physiologically acceptable liquid carrier. In some embodiments using separate microspheres of the active ingredients, the microspheres are mixed together in the liquid carrier. In other embodiments, each type of microsphere is separately mixed with a liquid carrier. In some embodiments, the microsphere suspension is then injected subcutaneously just below the dermis in 1.0 ml aliquots to cover about 2.0 $cm^2$ area per ml of the microsphere suspension, for example, for the treatment of cellulite. In some embodiments, about 10 to about 20 injections are administered to cover an area of from about 20 $cm^2$ to about 40 $cm^2$. Larger and/or smaller areas are treated in various embodiments. Alternatively, in some embodiments, bolus injections of 1.0 ml to 10.0 ml are injected into fat accumulations, such as the submental regions, lateral hips, and buttocks. Alternatively, injections as described above are made separately and sequentially in the same locations using two microsphere formulations encapsulating each active ingredient.

In some embodiments, needle-less injection is used to administer the microparticulate formulations as suspensions or as powdered loaded microparticles, i.e., without a liquid carrier.

PLGA microspheres encapsulate hydrophobic compounds more readily than hydrophilic compounds. To increase loading of hydrophilic active ingredients, in some embodiments, the microspheres are modified with polyethylene glycol units, as discussed above. Microspheres of certain sizes are substantially not absorbed into the blood or removed by lymph, thereby providing localized release of the active ingredient(s) within a target region. For example, in some embodiments, the microspheres are about 20 µm to about 200 µm in diameter, e.g., about 30 µm to about 175 µm, about 50 µm to about 150 µm, about 75 µm to about 125 µm, or any other diameter from about 20 µm to about 200 µm. The size of the microsphere also affects the release profile of the active ingredient(s) in the tissue. In general, larger microspheres provide a longer and more uniform release profile. Accordingly, in some embodiments, the average particle size in the formulation will be selected based on the desired release duration.

In an exemplary embodiment, a sustained release formulation comprises about 0.5 mg to about 7.5 mg (e.g., about 0.7 mg, 1 mg, 1.5 mg, 2.0 mg, 2.5 mg, 3 mg, 3.5 mg, 4 mg, 4.5 mg, 5 mg, 5.5 mg, 6 mg, 6.5 mg, 7 mg, or any other amount from about 0.5 mg to about 7.5 mg) of a compound of Formula I or Formula II, optionally about 1.5 mg to about 7.5 mg (e.g., about 2 mg, 2.5 mg, 3 mg, 3.5 mg, 4 mg, 4.5 mg, 5 mg, 5.5 mg, 6 mg, 6.5 mg, 7 mg, or any other amount from about 1.5 mg to about 7.5 mg) of dexamethasone, fluticasone, and/or budesonide, and also optionally about 1.5 mg to about 7.5 mg (e.g., about 2 mg, 2.5 mg, 3 mg, 3.5 mg, 4 mg, 4.5 mg, 5 mg, 5.5 mg, 6 mg, 6.5 mg, 7 mg, or any other amount from about 1.5 mg to about 7.5 mg) of deoxycholic acid or a pharmaceutically or cosmetically acceptable salt, solvate, prodrug, or ester thereof encapsulated in about 100 milligrams of polylactide glycolide (PLGA) copolymer microspheres at a ratio of about 70 lactide:30 glycolide. The amount of each active ingredient in the sustained release formulation depends on the period of controlled/sustained release required (about 3 days to about 12 months, e.g., 4 days, 5 days, 7 days, 10 days, 1 month, 45 days, 2 months, 3 months, 6 months, 8 months, 9 months, or any other release period from about 3 days to about 12 months).

In some embodiments, the subject to be treated is provided a non-sustained release formulation. In some embodiments, the non-sustained release formulation, after a single dose, provides activity for a duration from about 4 hours to about 24 hours, e.g., about 6 hours, 8 hours, 10 hours, 12 hours, 16 hours, 18 hours, 21 hours, or any other duration from about four hours to about 24 hours.

While certain embodiments have been described, these embodiments have been presented by way of example only, and are not intended to limit the scope of the disclosure. The formulations, methods, and kits described herein may be embodied in a variety of other forms. Furthermore, various omissions, substitutions and changes in the form of the formulations, methods, and kits described herein may be made without departing from the spirit of this disclosure. The accompanying claims and their equivalents are intended to cover such forms or modifications.

Example 1

Effect of Sodium Tetradecyl Sulfate on the Inguinal-Lateral Fat Pad (ILFP) of Hamsters Effect of sodium tetradecyl sulfate (0.5%, 1% or 3%) will be studied on the inguinal-lateral fat pad (ILFP) of hamsters
Species: Syrian golden hamsters
No of animals: 48 males (3 groups of 16)
Study: Hamsters will receive treatments into the right ILFP and saline into the left ILFP. Each set of injections consists of:
Two injections of sodium tetradecyl sulfate (one in the medial and one in the lateral portion of the right ILFP).
Two injections of 0.9% saline (one in medial and one in lateral portion of the left ILFP).

The sodium tetradecyl sulfate concentration to be assigned to each dose group (N:16 each) is 0.5, 1, or 3%. Injection volume will be 0.2 mL per injection. In each dose group, a subgroup ('c') of six animals will receive a second set of injections at 14 days after the first set (see below).

Fat pads will be harvested according to subgroups of each of the dose groups:
Subgroup 'a' (N=4): 4 hours post-treatment.
Subgroup 'b' (N=6): Day 14 post-treatment.
Subgroup 'c' (N=6): Day 28 after first treatment (2 weeks after second treatment on day 14).

The harvested right and left fat pads will be weighed (medial and lateral together) and frozen on dry ice. The medial and lateral portions of each fat pad will be separated and stored in a freezer. Selected medial pads will be analyzed histologically.

Dose Groups:
Group 1 (N=16): 0.5% sodium tetradecyl sulfate (2 injections, right medial and lateral)
Group 2 (N=16): 1% sodium tetradecyl sulfate (2 injections, right medial and lateral)
Group 3 (N=16): 3% sodium tetradecyl sulfate (2 injections, right medial and lateral)
All will receive contralateral saline (2 injections, left medial and lateral)
Subgroups from each dose group:
Subgroup 'a' (N=4): Treatment Day 0, harvest 4 hours.
Subgroup 'b' (N=6): Treatment Day 0, harvest Day 14.
Subgroup 'c' (N=6): Treatment Day 0 and 14, harvest Day 28.

Regimen:

TABLE 1

| Group | N | Dose (Conc) | Dose Volume | Injection Day | Tissue Collection |
|---|---|---|---|---|---|
| 1a | 4 | 0.5% | 0.2 mL × 2 inj | Day 0 | 4 hours |
| 1b | 6 | 0.5% | 0.2 mL × 2 inj | Day 0 | Day 14 |
| 1c | 6 | 0.5% | 0.2 mL × 2 inj | Day 0 & 14 | Day 28 |
| 2a | 4 | 1% | 0.2 mL × 2 inj | Day 0 | 4 hours |
| 2b | 6 | 1% | 0.2 mL × 2 inj | Day 0 | Day 14 |
| 2c | 6 | 1% | 0.2 mL × 2 inj | Day 0 & 14 | Day 28 |
| 3a | 4 | 3% | 0.2 mL × 2 inj | Day 0 | 4 hours |
| 3b | 6 | 3% | 0.2 mL × 2 inj | Day 0 | Day 14 |
| 3c | 6 | 3% | 0.2 mL × 2 inj | Day 0 & 14 | Day 28 |

Histology: From each subgroup, 4 right (sodium tetradecyl sulfate-treated) medial injection sites and 2 left (saline-treated) sites from each subgroup will be analyzed histologically by Zyagen [total 54 specimens analyzed]. Selection of individual sodium tetradecyl sulfate specimens will be based on degree of fat mass loss.

Example 2

Treatment of Fat Deposits with Compositions Comprising Sodium Tetradecyl Sulfate and Sodium Deoxycholate Primary human adipocytes will be incubated with varying concentrations of sodium tetradecyl sulfate and synthetic sodium deoxycholate synthesized using 9-HAD as starting material or bovine-derived sodium deoxycholate obtained from Sigma as described below.

Materials

Adipocytes (Zen-Bio cat #SA-1096), 96 well plates (US Scientific cat #cellstar no. 655180), Serum-free RPMI medium (Mediatech cat #17-105-CV), sodium tetradecyl sulfate, Sodium deoxycholate (DC) (Sigma cat #D6750), Synthetic Sodium glycodeoxycholate, PBS, MTS assay kit (Promega cat #G3580)

Adipocytes will arrive differentiated and at a density of 13,000 cells per well in a 96 well plate. Two plates will be received and each treated with the same samples. Cells will be incubated for 24 hours at 37° C. with 5% $CO_2$. A 1% stock solution of each bile acid (synthetic and non-synthetic DCA) will be made by dissolving 20 mg into 2 mL media (serum-free). Using the 1% stock solution, the following 11 solutions are prepared by dilution: 0.005%, 0.01%, 0.015%, 0.02%, 0.025%, 0.03%, 0.035%, 0.04%, 0.05%, 0.06%, and 0.1%, as well as 0% (media only).

Cells will be washed 2 times with 150 µL of room temperature 1x PBS (phosphate buffered saline). Media and then PBS will be removed from the wells in a 96 well plate by turning the plate upside down and decanting the liquid into a container. After the last PBS wash, 80 µL of sample will be added per well. Each concentration of a specific bile acid will be added to 8 wells and will be incubated for 1 hour at 37° C. with 5% $CO_2$. Plates will be removed from incubator and solution decanted. A 100 µL solution of will be diluted (40 µL in 1 mL of RPMI) MTS reagent (3-(4,5-dimethylthiazol-2-yl)-5-(3-carboxymethoxyphenyl)-2-(4-sulfophenyl-)-2H-tetrazolium, inner salt) will be added directly to each well. Plates will be incubated at 37° C. with 5% $CO_2$ until control (no bile acid) wells change color to orange-brown and then loaded onto a spectrophotometer that analyzes 96 well plates. Samples will be run at 490 nm wavelength setting.

Example 3

Phase III Clinical Study

A multicenter, phase III, randomized, double-blind, placebo-controlled, parallel-group study will be used to evaluate the efficacy and safety of sodium tetradecyl sulfate administered at fixed doses of 0.5% W/V and 1.0% W/V. The study will be divided into a screening period (week 1-8 to baseline; visit 1), followed by a 12-week treatment period (visits 2-5) and a 1.2-week efficacy and safety follow-up period (visits 6 and 7).

Inclusion and Exclusion Criteria

Men and women aged 18-65 years are eligible to participate if they present with moderate or severe submental fat ("SMF") [grade 2 or 3 on the 5-point Clinician-Reported Submental Fat Rating Scale (CR-SMFRS)] and express dissatisfaction with the appearance of their submental area [Subject Self-Rating Scale (SSRS) score 0-3] at visit 2. Patients will agree to undergo clinical evaluations and laboratory tests and to maintain stable body weight, diet and exercise practices during the study. Women of reproductive age will be required not to be pregnant or lactating and to practice birth control during the study. The principal exclusion criteria will be: previous intervention to treat SMF; anatomical features or previous trauma liable to interfere with SMF evaluation or result in an aesthetically unacceptable outcome after treatment; evidence of any cause of submental enlargement other than SMF; and any medical condition likely to affect safety or efficacy assessments or the patient's ability to undergo study procedures or provide informed consent. Patients with a body mass index (BMI) >30 kg m$^{-2}$, those undergoing or considering a weight-reduction program, and patients with a history of sensitivity to any components of the study material or topical or local anesthetics will also be excluded.

Randomization

Patients will be randomized (1:1:1) at visit 2, after completion of baseline evaluations, through allocation of a unique randomization number using a computerized web/voice-response system. Sodium tetradecyl sulfate and placebo treatment kits will have an identical appearance and carry a blinded label with a random kit number; these will be assigned to patients using the computerized system.

Interventions

All randomized patients will have at least one treatment session, with a maximum of four sessions, separated by 28±5 day intervals (visits 2-5), Patients will receive up to 10 mL of the study drug per treatment session, and the number of sessions will be dependent on the amount of remaining SMF and each patient's satisfaction with the appearance of their face and chin. Injections will be administered subcutaneously directly into the pre-platysmal SMF at a volume of 0.2 ml per injection and spaced approximately 1 cm apart using a grid to provide even coverage. Topical anesthesia will be provided, if needed. Premature treatment discontinuation could occur owing to adverse events (AEs), early therapeutic success or at the patient's request. The treatment area will be evaluated 7±3 days after each treatment and concomitant medication use was reported, Patients will attend two follow-up visits (visits 6 and) 4 weeks (±5 days) and 12 weeks (±7 days) after the final treatment session.

Efficacy Outcome Measures

Efficacy endpoints will be evaluated at visit 7 (12 weeks after final treatment). There will be two co-primary efficacy endpoints: the proportion of treatment responders, i.e. with a reduction in SMF of ≥1 point on the 5-point CR-SMFRS relative to baseline, and the proportion of patients satisfied with their appearance in association with their face and chin with a score of ≥4 on the 7-point SSRS rating scale). To confirm the primary endpoint results, sensitivity analyses will be conducted on the secondary parameters of change from baseline in CR-SMFRS and SSRS scores, and changes in caliper measurements of SMF thickness, by treatment session. The effect of treatment on skin laxity (Skin Laxity Rating Scale, SLRS) will also be evaluated, and patient-reported outcomes will be assessed using the Patient-Reported Submental Fat Rating Scale (PR-SMFRS) and Patient-Reported Submental Impact Scale (PR-SMFIS). Additional patient-reported instruments will also be used.

Safety Outcome Measures

Adverse effects (AE) will be evaluated at each visit and approximately 7 days after each treatment session, and will be characterized descriptively by the day on which they started and stopped, and by severity and intensity. Treatment-emergent AEs will be defined as those with onset or exacerbation after the first treatment dose. Changes from baseline in clinical laboratory parameters and other tests, and variations in vital signs, body temperature and body weight, will also be measured.

Statistical Methodology

Using 80% of the effect size observed in two previous placebo-controlled and a 10% dropout rate per treatment group with a Pearson chi-square test for two proportions (two-sided test with $\alpha=0.025$), a conservatively rounded sample size of 120 patients per treatment group be used to guarantee a power of 90%.

The efficacy analyses will be based on the intention-to-treat population (all randomized patients who had at least one efficacy assessment at baseline), with missing values at visit 7 imputed using last observation carried forward. The null hypothesis for the treatment comparisons is that there is no difference between each dose of sodium tetradecyl sulfate and placebo for the two co-primary efficacy endpoints. Comparisons of the two sodium tetradecyl sulfate dose groups with placebo will be made via odds ratios from binary logistic regression. An adjustment for multiplicity will be performed. Because there will be two co-primary endpoints, the null hypotheses for both variables will be rejected at the same significance level ($\alpha=0.05$). This will be accounted for by using the larger of the two P-values in the Bonferroni-Holm procedure.

For the secondary endpoints, changes from baseline in CR-SMFRS and caliper scores will be analyzed using a mixed-models repeated-measures analysis. Changes from baseline in SSRS scores will be analyzed by an analysis of variance (ANOVA). PR-SMFRS improvements of ≥1 point are analyzed by binary logistic regression. Changes from baseline in SLRS scores will be recorded in frequency tables and Pearson's chi-square test will be applied to compare each sodium tetradecyl sulfate group with placebo. Descriptive statistics will be calculated for PR-SMFIS scores, with the change from baseline analyzed by a post hoc Fisher's least-square difference test for continuous variables, only if ANOVA shows an overall treatment effect. Statistical summaries for AEs will be based on treatment-emergent AEs in the safety population (all patients who received at least one treatment with study drug). The numbers of AEs and patients presenting with each AE will be categorized according to association with treatment, study withdrawal, death, severity, intensity, system organ class, and preferred term.

The examples and embodiments described herein are for illustrative purposes only and various modifications or changes are included within the spirit and purview of this application and scope of the appended claims. All publications, patents, and patent applications cited herein are hereby incorporated by reference for all purposes.

What is claimed is:

1. A method for reducing localized subcutaneous fat, comprising subcutaneously injecting into a human or animal subject a formulation, comprising:
   a. a therapeutically or cosmetically effective amount of tetradecyl sulfate, or a pharmaceutically or cosmetically acceptable salt, solvate, prodrug, or ester thereof; and
   b. a liquid carrier,
   wherein the tetradecyl sulfate is present in an amount from about 0.5% to 3% w/v.

2. A method for the reduction and/or prevention of localized subcutaneous adipose tissue comprising administering to a human or animal subject by subcutaneous injection a formulation comprising tetradecyl sulfate, or a pharmaceutically or cosmetically acceptable salt, solvate, prodrug, or ester thereof in an amount from about 0.5% to 5% w/v, and a liquid carrier.

3. The method of claim 1, wherein the tetradecyl sulfate is sodium tetradecyl sulfate.

4. The method of claim 1, further comprising propylene glycol.

5. The method of claim 1, wherein the tetradecyl sulfate is micronized.

6. The method of claim 1, further comprising a microparticulate and/or nanoparticulate carrier.

7. The method of claim 1, wherein the formulation is stable for a period of at least 6 months at a temperature of about 0° C. to about 50° C.

8. The method of claim 1, further comprising an alcohol having 3 to 7 carbon atoms is present in an amount from about 0.5% w/v to about 10% w/v.

9. The method of claim 1, further comprising an alcohol having 3 to 7 carbon atoms is present in an amount of approximately 2% w/v.

10. The method of claim 1, wherein the tetradecyl sulfate is present in an amount of 0.5%, 1%, or 3%.

11. The method of claim 1, wherein the formulation has a pH of about 6 to 10.

12. The method of claim 1, wherein the formulation has a pH of about 7 to 8.

13. The method of claim 1, wherein the injection volume is less than about 2 ml.

14. The method of claim 1, wherein the injection volume is less than about 1.4 ml.

15. The method of claim 1, wherein the injection volume is less than about 0.5 ml.

16. The method of claim 1, wherein the subcutaneous injection is injection into the submental region of a person.

17. The method of claim 1, wherein the subcutaneous injection is injection into the periorbital region of a person.

18. The method of claim 1, wherein the subcutaneous injection is injection into the intraorbital region of a person.

19. The method of claim 1, wherein the subcutaneous injection is injection into the abdominal region of a person.

20. The method of claim 1, wherein the subcutaneous injection is injection into a fat pad.

21. The method of claim 2, wherein the tetradecyl sulfate is present in an amount of 0.5%, 1%, or 3%.

22. The method of claim 1, wherein the subcutaneous injection is injection into the middle to upper area of the upper arm of a person.

23. The method of claim 1, wherein the subcutaneous injection is injection into the lower back or upper back.

* * * * *